United States Patent
Bian et al.

(10) Patent No.: US 12,357,641 B2
(45) Date of Patent: Jul. 15, 2025

(54) IDENTIFICATION OF OLEANOLIC ACID AND PLANT EXTRACT FOR GLUCOSE-6-PHOSPHATE DEHYDROGENASE-RELATED DISORDERS INCLUDING BAG3OPATHY

(71) Applicant: Hong Kong Baptist University, Hong Kong (CN)

(72) Inventors: Zhaoxiang Bian, Hong Kong (CN); Tao Hung, Hong Kong (CN); Ling Zhao, Hong Kong (CN); Lidan Zhong, Hong Kong (CN); Chengyuan Lin, Hong Kong (CN)

(73) Assignee: Hong Kong Baptist University, Hong Kong (CN)

( * ) Notice: Subject to any disclaimer, the term of this patent is extended or adjusted under 35 U.S.C. 154(b) by 96 days.

(21) Appl. No.: 18/046,194

(22) Filed: Oct. 13, 2022

(65) Prior Publication Data
US 2024/0148751 A1     May 9, 2024

(51) Int. Cl.
*A61K 31/56* (2006.01)
*A61K 36/732* (2006.01)
*A61P 9/00* (2006.01)

(52) U.S. Cl.
CPC ............ *A61K 31/56* (2013.01); *A61K 36/732* (2013.01); *A61P 9/00* (2018.01)

(58) Field of Classification Search
CPC ......... A61K 31/56; A61K 36/732; A61P 9/00; A61P 21/00; A61P 25/28
See application file for complete search history.

(56) References Cited

U.S. PATENT DOCUMENTS

2019/0076381 A1*   3/2019   Newman ................ A61K 31/56

FOREIGN PATENT DOCUMENTS

| CN | 102229638 A | 11/2011 |
| JP | 2000247993 A | 9/2000 |

OTHER PUBLICATIONS

Schröder et al (Brain Pathology, 2009; 19:483-492) (Year: 2009).*
Garcia et al (Trends in Pharmacological Sciences, 2021; 42(10):829-844) (Year: 2021).*
Koperniku et al (J Med Chem, 2022; 65:4403-4423) (Year: 2022).*
Liu et al (Heart Failure Reviews, 2021; 26:183-194) (Year: 2021).*
Tian et al (Journal of Planar Chromatography, 2015; 28(6):443-447) (Year: 2015).*
International Search Report and Written Opinion of PCT application No. PCT/CN2023/123896 issued from the International Search Authority on Dec. 21, 2023.

* cited by examiner

*Primary Examiner* — Rayna Rodriguez
(74) *Attorney, Agent, or Firm* — S&F/WEHRW

(57) ABSTRACT

A method of treating a glucose-6-phosphate dehydrogenase deregulated disorder in a subject in need thereof, the method involving administering a therapeutically effective amount of oleanolic acid or a conjugate salt thereof or prodrug thereof to the subject. The glucose-6-phosphate dehydrogenase deregulated disorder can be BCL2 associated athanogene myofibrillar myopathy, amyotrophic lateral sclerosis, Huntington disease, Parkinson disease, or Alzheimer disease.

9 Claims, 15 Drawing Sheets
Specification includes a Sequence Listing.

Bag3 protein

WT human HQLPRGYIS I PV IHEQNVTRP
mouse HQLPRGYIP I PV IHEQNITRP

Bag3opathy human HQLPRGYIS I LV IHEQNVTRP
mouse HQLPRGYIP I LV IHEQNITRP

SEQUENCE LISTING

```
Sequence total quantity: 8
SEQ ID NO: 1            moltype = AA  length = 575
FEATURE                 Location/Qualifiers
source                  1..575
                        mol_type = protein
                        organism = Homo sapiens
SEQUENCE: 1
MSAATHSPMM QVASGNGDRD PLPPGWEIKI DPQTGWPFFV DHNSRTTTWN DPRVPSEGPK  60
ETPSSANGPS REGSRLPPAR EGHPVYPQLR PGYIPIPVLH EGAENRQVHP FHVYPQPGMQ  120
```

```
RFRTEAAAAA PQRSQSPLRG MPETTQPDKQ CGQVAAAAAA QPPASHGPER SQSPAASDCS   180
SSSSSASLPS SGRSSLGSHQ LPRGYISIPV IHEQNVTRPA AQPSFHQAQK THYPAQQGEY   240
QTHQPVYHKI QGDDWEPRPL RAASPFRSSV QGASSREGSP ARSSTPLHSP SPIRVHTVVD   300
RPQQPMTHRE TAPVSQPENK PESKPGPVGP ELPPGHIPIQ VIRKEVDSKP VSQKPPPPSE   360
KVEVKVPPAP VPCPPPSPGP SAVPSSPKSV ATEERAAPST APAEATPPKP GEAEAPPKHP   420
GVLKVEAILE KVQGLEQAVD NFEGKKTDKK YLMIEEYLTK ELLALDSVDP EGRADVRQAR   480
RDGVRKVQTI LEKLEQKAID VPGQVQVYEL QPSNLEADQP LQAIMEMGAV AADKGKKNAG   540
NAEDPHTETQ QPEATAAATS NPSSMTDTPG NPAAP                             575

SEQ ID NO: 2           moltype = AA  length = 577
FEATURE                Location/Qualifiers
source                 1..577
                       mol_type = protein
                       organism = Mus musculus
SEQUENCE: 2
MSAATQSPMM QMASGNGASD RDPLPPGWEI KIDPQTGWPF FVDHNSRTTT WNDPRVPPEG    60
PKDTASSANG PSRDGSRLLP IREGHPIYPQ LRPGYIPIPV LHEGSENRQP HLFHAYSQPG   120
VQRFRTEAAA ATPQRSQSPL RGGMTEAAQT DKQCGQMPAT ATTAAAQPPT AHGPERSQSP   180
AASDCSSSSS SASLPSSGRS SLGSHQLPRG YIPIPVIHEQ NITRPAAQPS FHQAKTHYP    240
AQQGEYQPQQ PVYHKIQGDD WEPRPLRAAS PFRSPVRGAS SREGSPARSG TPVHCPSPIR   300
VHTVVDRPQP MTHREPPPVT QPENKPESKP GPAGPDLPPG HIPIQVIRRE ADSKPVSQKS   360
PPPAEKVEVK VSSAPIPCPS PSPAPSAVPS PPKNVAAEQK AAPSPAPAEP AAPKSGEAET   420
PPKHPGVLKV EAILEKVQGL EQAVDSFEGK KTDKKYLMIE EYLTKELLAL DSVDPEGRAD   480
VRQARRDGVR KVQTILEKLE QKAIDVPGQV QVYELQPSNL EAEQPLQEIM GAVVADKDKK   540
GPENKDPQTE SQQLEAKAAT PPNPSNPADS AGNLVAP                           577

SEQ ID NO: 3           moltype = AA  length = 21
FEATURE                Location/Qualifiers
source                 1..21
                       mol_type = protein
                       organism = Homo sapiens
SEQUENCE: 3
HQLPRGYISI LVIHEQNVTR P                                             21

SEQ ID NO: 4           moltype = AA  length = 21
FEATURE                Location/Qualifiers
source                 1..21
                       mol_type = protein
                       organism = Mus musculus
SEQUENCE: 4
HQLPRGYISI LVIHEQNVTR P                                             21

SEQ ID NO: 5           moltype = DNA  length = 29
FEATURE                Location/Qualifiers
source                 1..29
                       mol_type = genomic DNA
                       organism = Mus musculus
SEQUENCE: 5
cccatccccg tgatacatga gcagaatat                                     29

SEQ ID NO: 6           moltype = DNA  length = 29
FEATURE                Location/Qualifiers
source                 1..29
                       mol_type = genomic DNA
                       organism = Mus musculus
SEQUENCE: 6
cccatcctcg tgatacatga gcagaatat                                     29

SEQ ID NO: 7           moltype = DNA  length = 24
FEATURE                Location/Qualifiers
source                 1..24
                       mol_type = genomic DNA
                       organism = Mus musculus
SEQUENCE: 7
ggagtggtgc tggagattga aacc                                          24

SEQ ID NO: 8           moltype = DNA  length = 23
FEATURE                Location/Qualifiers
source                 1..23
                       mol_type = genomic DNA
                       organism = Mus musculoides
SEQUENCE: 8
gaagcacctc tgacgggtga cct                                           23
```

IDENTIFICATION OF OLEANOLIC ACID AND PLANT EXTRACT FOR GLUCOSE-6-PHOSPHATE DEHYDROGENASE-RELATED DISORDERS INCLUDING BAG3OPATHY

REFERENCE TO SEQUENCE LISTING

The Sequence Listing identified as Sequence_Listing_P24623US00.xml; Size: 8,814 bytes; and Date of Creation: Oct. 11, 2022, filed herewith, is hereby incorporated by reference in its entirety.

TECHNICAL FIELD

The present disclosure relates to the use of oleanolic acid and oleanolic acid containing plants, such as *Chaenomelis fructus*, and extracts thereof for the treatment of glucose-6-phosphate dehydrogenase (G6PD) deregulated disorders, such as BCL2 associated athanogene 3 related myofibrillar myopathy (Bag3opathy), amyotrophic lateral sclerosis, Huntington disease, Parkinson disease, and Alzheimer disease.

BACKGROUND

Myofibrillar myopathies (MFMs) are a group of chronic neuromuscular disorders characterized by disintegration of Z-disk, accumulation of myofibrillar degradation products, and mitochondrial abnormalities. MFMs cause progressive muscle weakness in patients, frequently associated with cardiomyopathy and neuropathy. With distinct morphology, MFM are genetically heterogeneous: mutations in several genes have been implicated in MFM, including the desmin gene (DES), the alphaB-crystallin gene (CRYAB), myotilin (MYOT), Z-band alternatively spliced PDZ-motif (ZASP), filamin C (FLNC), BCL2 Associated Athanogene 3 (BAG3), plectin (PLEC), Four And A Half LIM Domains 1 (FHL1), DnaJ Heat Shock Protein Family (Hsp40) Member B6 (DNAJB6), and titin (TTN). In particular, Bag3opathy is associated with childhood onset, severe muscle weakness, cardiomyopathy, and respiratory insufficiency.

BAG3 is a member of BAG family of co-chaperones, strongly expressed in skeletal and cardiac muscles. It interacts with the heat shock protein 70 (Hsp70) through BAG domain and other binding partners via the WW domain. BAG3 is involved in many biological processes, including apoptosis, cytoskeleton organization, autophagy, and development, as well as adaptive response to stressful stimuli. Initially, BAG3 knock-out in mice was shown to result in fulminant myopathy and early lethality. In 2009, Selcen et al. firstly identified Bag3opathy in three MFM patients. To date, less than twenty Bag3opathy patients have been reported worldwide, while only one of them is from a Chinese family.

Most Bag3opathy cases are caused by mutation c.626C>T, p.Pro209Leu (P209L), which could interrupt the crucial interactions between BAG3 and small heat shock proteins, including HspB8, HspB6, and CRYAB. Two mechanisms have been proposed to contribute to the pathogenesis of Bag3opathy: (1) chaperone-assisted selective autophagy (CASA), where BAG3 works with HspB8 and Hsc70 to facilitate the degradation of damaged components upon muscle contraction; and (2) maintaining myofibrillar integrity under mechanical stress through BAG3 and Hsc70 interacting with actin capping protein CapZ. Despite of these findings, the pathogenesis of Bag3opathy are still largely unclear, and no causative therapy is available.

The thus exists a need to develop improved methods of treating G6PD deregulated disorders, such as Bag3opathy, amyotrophic lateral sclerosis, Huntington disease, Parkinson disease, and Alzheimer Disease.

SUMMARY

The present disclosure relates to the use of oleanolic acid, and any plant extract comprising oleanolic acid, such as *Chaenomelis fructus*, for treating for G6PD deregulated disorders, such as Bag3opathy, amyotrophic lateral sclerosis, Huntington disease, Parkinson disease, and Alzheimer Disease.

In a first aspect, provided herein is a method of treating a glucose-6-phosphate dehydrogenase (G6PD) deregulated disorder in a subject in need thereof, the method comprising administering a therapeutically effective amount of oleanolic acid, a conjugate salt thereof, or a prodrug thereof to the subject.

In certain embodiments, the G6PD deregulated disorder is selected from the group consisting of BCL2 associated athanogene myofibrillar myopathy (Bag3opathy), amyotrophic lateral sclerosis, Huntington disease, Parkinson disease, and Alzheimer disease.

In certain embodiments, the G6PD deregulated disorder is BCL2 associated athanogene myofibrillar myopathy (Bag3opathy).

In certain embodiments, the subject suffers from one or more of severe muscle weakness, cardiomyopathy, and respiratory insufficiency.

In certain embodiments, the oleanolic acid or a conjugate salt thereof is administered to the subject in the form of a botanical product or an extract thereof.

In certain embodiments, the botanical product comprises one or more of *Crataegi fructus, Forsythiae fructus, Prunellae spica, Verbenae herba, Eriobotryae folium, Ligustri lucidi fructus, Kaki calyx, Chaenomelis fructus, Jujubae fructus, Comi fructus*, or an extract thereof.

In certain embodiments, the botanical product comprises *Chaenomelis fructus* or an extract thereof.

In certain embodiments, the *Chaenomelis fructus* extract is prepared by contacting *Chaenomelis fructus* with ethanol thereby extracting at least a portion of the oleanolic acid or a conjugate salt thereof present in the *Chaenomelis fructus* and forming an ethanol extract comprising oleanolic acid or a conjugate salt thereof and optionally removing ethanol from the ethanol extract thereby forming the *Chaenomelis fructus* extract.

In certain embodiments, the subject has a BCL2 Associated Athanogene 3 (BAG3) gene comprising a c.626C>T mutation.

In certain embodiments, the prodrug of oleanolic acid has the chemical formula 2:

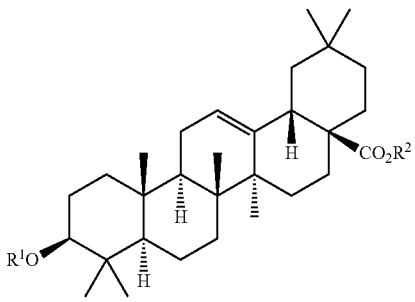

or a pharmaceutically acceptable salt thereof, wherein
R$^1$ is hydrogen, R(C=O)— or RO(C=O)—;
R$^2$ is hydrogen, alkyl, cycloalkyl, aralkyl, or aryl; and
R for each instance is independently hydrogen, alkyl, aralkyl, aryl, or heterocycloalkyl, wherein at least one R$^1$ and R$^2$ is not hydrogen.

In certain embodiments, the subject is a human.

In a second aspect, provided herein is a method of treating BCL2 associated athanogene myofibrillar myopathy (Bag3opathy) in a subject in need thereof, the method comprising administering a therapeutically effective amount of oleanolic acid, a conjugate salt thereof, or a prodrug thereof to the subject.

In certain embodiments, the oleanolic acid or a conjugate salt thereof is administered to the subject in the form of a botanical product or an extract thereof.

In certain embodiments, the botanical product comprises one or more of *Crataegi fructus*, *Forsythiae fructus*, *Prunellae spica*, *Verbenae herba*, *Eriobotryae folium*, *Ligustri lucidi fructus*, *Kaki calyx*, *Chaenomelis fructus*, *Jujubae fructus*, *Comi fructus*, or an extract thereof.

In certain embodiments, the botanical product comprises *Chaenomelis fructus* or an extract thereof.

In certain embodiments, the *Chaenomelis fructus* extract is prepared by contacting *Chaenomelis fructus* with ethanol thereby extracting at least a portion of the oleanolic acid or a conjugate salt thereof present in the *Chaenomelis fructus* and forming an ethanol extract comprisng oleanolic acid or a conjugate salt thereof and optionally removing ethanol from the ethanol extract thereby forming the *Chaenomelis fructus* extract.

In certain embodiments, the subject has a BCL2 Associated Athanogene 3 (BAG3) gene comprising a c.626C>mutation.

In certain embodiments, the prodrug of oleanolic acid has the chemical formula 2:

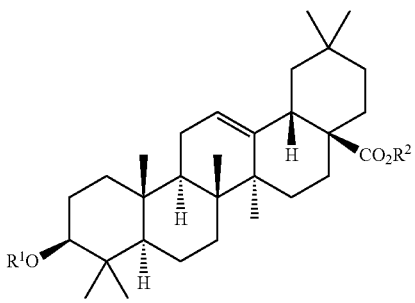

or a pharmaceutically acceptable salt thereof, wherein
R$^1$ is hydrogen, R(C=O)— or RO(C=O)—;
R$^2$ is hydrogen, alkyl, cycloalkyl, aralkyl, or aryl; and
R for each instance is independently hydrogen, alkyl, aralkyl, aryl, or heterocycloalkyl, wherein at least one R$^1$ and R$^2$ is not hydrogen.

In certain embodiments, the subject is a human.

Other aspects and advantages of the present disclosure will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 4 shows identification of mouse Bag3 protein mutation site that is equivalent to human Bag3opathy-causing mutation, P209L (residues 199 to 219 of SEQ ID NO: 1; residues 205 to 225 of SEQ ID NO: 2; SEQ ID NO: 3; and SEQ ID NO: 4).

DETAILED DESCRIPTION

Definitions

Figure 1:
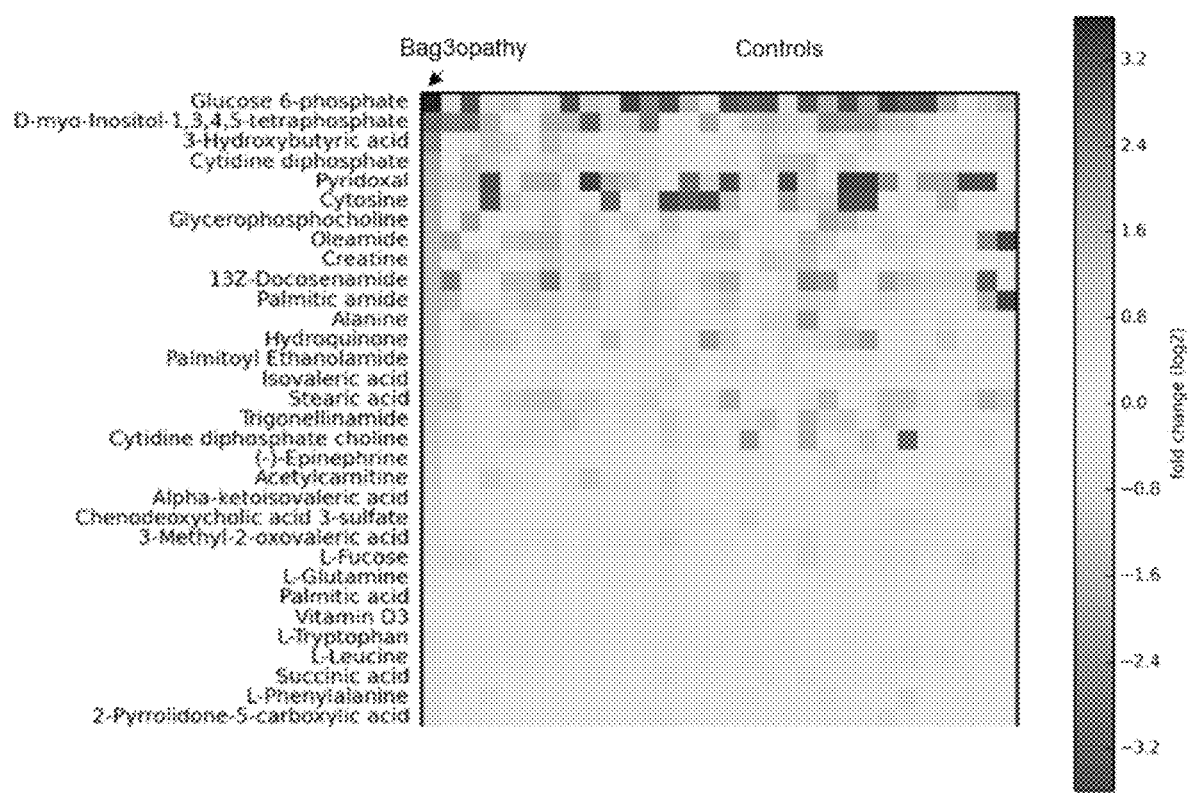
FIG. 1 shows serum metabolome analysis of Bag3opathy patient. Significantly changed metabolites in BAG3opathy patient and healthy controls.
Figure 1:
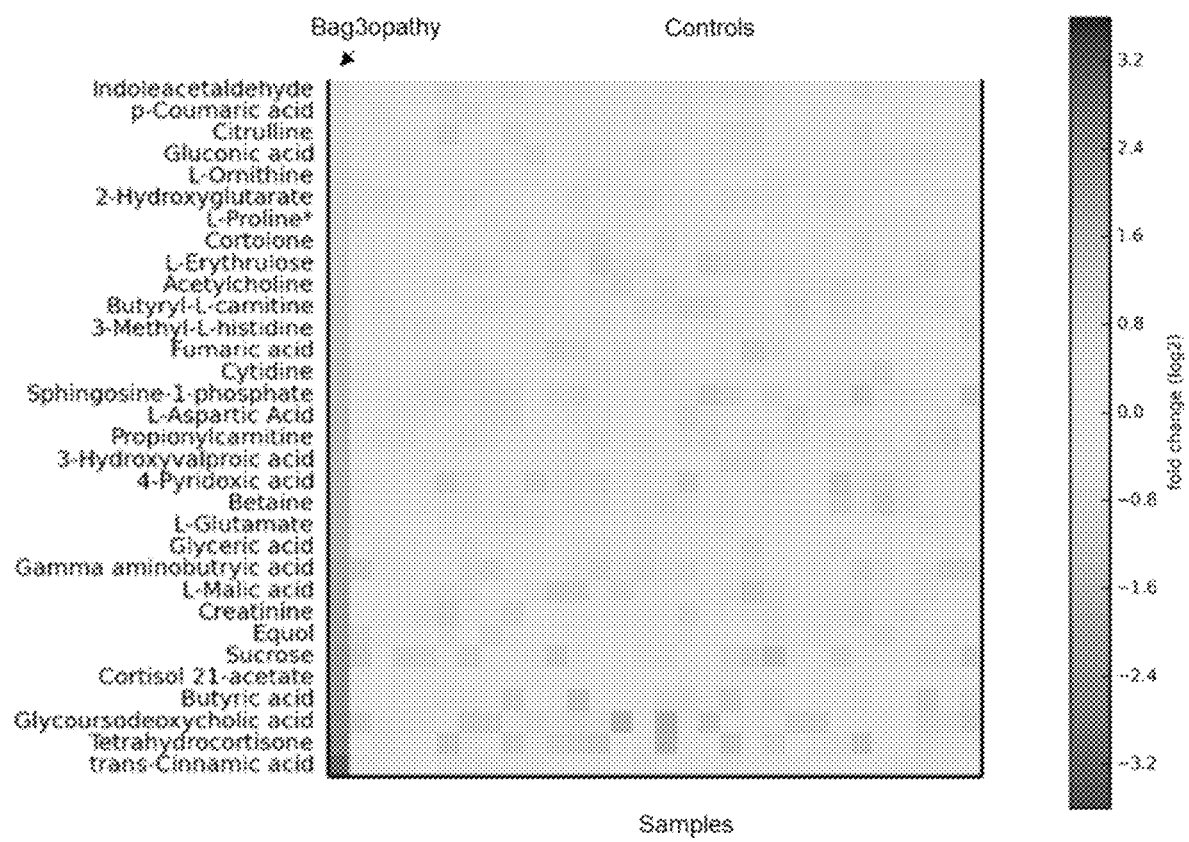

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "aralkyl" is art-recognized and refers to an alkyl group substituted with an aryl group (e.g., an aromatic or heteroaromatic group).

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocycloalkyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

The term "composition" is intended to encompass a product comprising the specified ingredients in the specified amounts, as well as any product that results, directly or indirectly, from combinations of the specified ingredients in the specified amounts.

As used herein, the term "isolated" in connection with a compound described herein means the compound is not in a botanical product and the compound is separated from some or all of the components that typically accompany it in a botanical product.

As used herein, the term "substantially pure" in connection with a sample of a compound described herein means the sample contains at least 60% by weight of the compound. In certain embodiments, the sample contains at least 70% by weight of the compound; at least 75% by weight of the compound; at least 80% by weight of the compound; at least 85% by weight of the compound; at least 90% by weight of the compound; at least 95% by weight of the compound; or at least 98% by weight of the compound.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, and rodents.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

Other definitions for selected terms used herein may be found within the detailed description of the present disclosure and apply throughout. Unless otherwise defined, all other technical terms used herein have the same meaning as commonly understood to one of ordinary skill in the art to which the invention belongs.

Provided herein is a method of treating a G6PD deregulated disorder in a subject in need thereof, the method comprising administering a therapeutically effective amount of oleanolic acid or a conjugate salt thereof or a prodrug thereof to the subject.

Oleanolic acid can be represented by a compound of Formula 1:

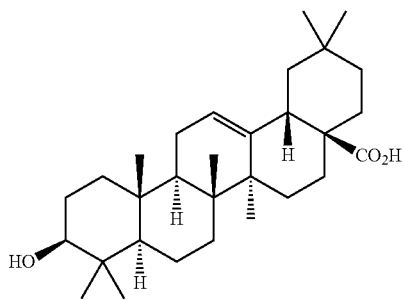

A prodrug refers to an inactive, or significantly less active, form of oleanolic acid, which after administration is metabolized in vivo into oleanolic acid and/or one or more active metabolites oleanolic acid. The prodrug may be formed using means generally known in the art, and therefore may take essentially any form that would be recognized to one of ordinary skill in the art. Prodrugs include, for example, oleanolic acid wherein the hydroxy or carboxy group is bonded to any group that, when the prodrug is administered to a subject, cleaves to form a free hydroxyl or free carboxylic acid, respectively. Examples include, but are not limited to, alkyl acyl ester and aryl acyl ester derivatives of the alcohol, such as acetate, formate, benzoate derivatives; alkyl carbonate and aryl carbonate derivatives of the alcohol, alkyl, carbocyclic, aryl and alkylaryl esters such as methyl, ethyl, propyl, iso-propyl, butyl, isobutyl, sec-butyl, tert-butyl, cyclopropyl, phenyl, benzyl and phenethyl esters and the like.

In certain embodiments, the prodrug of oleanolic acid is represented by a compound of Formula 2:

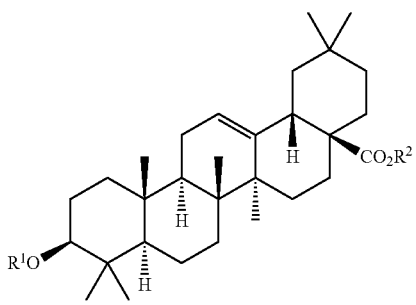

2 or a pharmaceutically acceptable salt thereof, wherein
R$^1$ is hydrogen, R(C=O)— or RO(C=O)—;
R$^2$ is hydrogen, alkyl, cycloalkyl, aralkyl, or aryl; and
R for each instance is independently hydrogen, alkyl, aralkyl, aryl, or heterocycloalkyl, wherein at least one R$^1$ and R$^2$ is not hydrogen.

In certain embodiments, R for each instance is independently hydrogen, $C_1$-$C_4$ alkyl, methyl, ethyl, isopropyl, n-propyl, t-butyl, benzyl, or phenyl.

The oleanolic acid or a conjugate salt thereof can be administered in isolated and/or substantially pure form or a botanical product comprising oleanolic acid or a conjugate salt thereof, an extract of a botanical product comprising oleanolic acid or a conjugate salt, or a pharmaceutical composition comprising any one or more of the foregoing.

The botanical product can be any botanical product comprising oleanolic acid.

The botanical product can include any constituent of a plant, higher plant, tree, algae, fungi, or combination thereof that contains or is suspected of containing one or more polysaccharides. The botanical product can include, but is not limited to, stems, leaves, bark, fruit, skin of fruit, vegetables, flowers, seeds, roots, rhizomes, legumes or any organic constituent of a plant or tree.

In certain embodiments, the plant is *Crataegi fructus, Forsythiae fructus, Prunellae spica, Verbenae herba, Eriobotryae folium, Ligustri lucidi fructus, Kaki calyx, Chaenomelis fructus, Jujubae fructus, Corni fructus*, or a mixture thereof. In certain embodiments, the plant is *Chaenomelis fructus*.

The extract of the botanical product can be prepared using well known methods in the art. In certain embodiments, the extract of the botanical product is prepared by bringing the botanical product in contact with a solvent thereby extracting at least a portion of the oleanolic acid or a conjugate salt thereof and forming an extraction solvent comprising oleanolic acid or a conjugate salt thereof; separating the botanical product and the extraction solvent; and optionally removing the solvent from the extraction solvent thereby forming the extract of the botanical product.

The botanical product can be extracted directly or can optionally pretreated by, e.g., mechanical pretreatment, such as mulching, shredding, chopping, milling, grinding, and/or sieving; and/or chemical pretreatment, such as acidic or basic extraction to remove impurities.

The solvent can comprise any solvent or mixture of solvents in which the oleanolic acid or a conjugate salt thereof is at least partially soluble. In certain embodiments, the solvent is an alcohol, an ester, an ether, a ketone, an aromatic solvent, an alkane, a formamide, a sulfoxide, alkyl halides, alkylnitriles, nitroalkanes, or a mixture thereof. In certain embodiments, the solvent is methanol, ethanol, isopropanol, n-propanol, acetone, ethyl acetate, diethyl ether, methyl tertbutyl ether, tetrahydrofuran (THF), 2-methyltetrahydrofuran, tetrahydropyran (THP), dioxane, 1,2,-dimethoxyether (DME), benzene, toluene, xylene, chlorobenzene, dichloromethane, dichloroethane, chloroform, acetonitrile, nitromethane, dimethyl sulfoxide (DMSO), dimethyl formamide (DME), N-methyl pyrrolidone (NMP), or a mixture thereof.

The solvent can comprise an alcoholic solvent comprising one or more $C_1$-$C_6$ aliphatic alcohols and an aqueous solvent comprising at least one salt. In certain embodiments, the alcoholic solvent comprises one or more $C_1$-$C_5$, $C_1$-$C_4$, $C_1$-$C_3$, or $C_2$-$C_3$, aliphatic alcohols. Exemplary $C_1$-$C_6$ aliphatic alcohols include, but are not limited to, methanol, ethanol, 1-proponol, isoproponol, n-butanol, isobutanol, sec-butanol, tert-butyl alcohol, 1-pentanol, isoamyl alcohol, 2-methyl-1-butanol, neopentyl alcohol, 2-pentanol, 3-methyl-2-butanol, 3-pentanol, tert-amyl alcohol, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, and 3,3-dimethyl-1-butanol. In certain embodiments, the alcoholic solvent comprises one or more of methanol, ethanol, 1-proponol, and isopropanol. In certain embodiments, the alcoholic solvent is ethanol.

The step of removing the solvent from the extraction solvent can be accomplished using well known methods known in the art, such as by evaporation, distillation e.g., under reduced pressure and/or heat, freeze drying, spray drying, fluid bed drying, direct oven heat drying, etc.

In certain embodiments, *Chaenomelis fructus* extract is prepared by bringing in to contact ethanol and *Chaenomelis fructus* thereby forming extracting at least a portion of the oleanolic acid or a conjugate salt thereof and forming an ethanol extract comprising oleanolic acid or a conjugate salt thereof; separating the ethanol extract from the *Chaenomelis fructus*; and optionally removing the ethanol from the ethanol extract thereby forming the *Chaenomelis fructus* extract.

The present disclosure also provides a pharmaceutical composition comprising oleanolic acid or a conjugate salt thereof or an herbal extract comprising oleanolic acid or a conjugate salt thereof and at least one pharmaceutically acceptable excipient and/or pharmaceutically acceptable carrier.

The oleanolic acid or an herbal extract comprising oleanolic acid and their pharmaceutically acceptable salts can be administered to a subject either alone or in combination with pharmaceutically acceptable carriers or diluents in a pharmaceutical composition according to standard pharmaceutical practice. The oleanolic acid or an herbal extract comprising oleanolic acid can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of oleanolic acid or an herbal extract comprising oleanolic acid or their pharmaceutically acceptable salts, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

Oleanolic acid contains acidic functional groups and, thus, is capable of forming pharmaceutically-acceptable salts with pharmaceutically-acceptable bases. The term "pharmaceutically-acceptable salts" in these instances refers to the relatively non-toxic, inorganic and organic base addition salts of oleanolic acid. These salts can likewise be prepared in situ in the administration vehicle or the dosage form manufacturing process, or by separately reacting the purified oleanolic acid in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising oleanolic acid or an herbal extract comprising oleanolic acid include the step of bringing into association oleanolic acid or an herbal extract comprising oleanolic acid with the carrier and, optionally, one or more accessory ingredients. In general, the formulations are prepared by uniformly and intimately bringing into association oleanolic acid or an herbal extract comprising oleanolic acid with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise oleanolic acid or an herbal extract comprising oleanolic acid in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars (such as sucrose), alcohols, non-ionic surfactants (such as Tween 20) antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The G6PD deregulated disorder can be selected from the group consisting of Bag3opathy, amyotrophic lateral sclerosis, Huntington disease, Parkinson disease, and Alzheimer disease. In certain embodiments, the G6PD deregulated disorder is Bag3opathy.

Virus infection, cardiovascular diseases (Meng et al. Frontiers in Pharmacology. 2022)

The subject can suffer from one or more of severe muscle weakness, cardiomyopathy, and respiratory insufficiency. In certain embodiments, the subject has a BAG3 gene comprising a c.626C>T mutation.

Specific routes of administration and the dosage regimen will be determined by skilled clinicians, based on factors such as the exact nature of the condition being treated, the severity of the condition, and the age and general physical condition of the patient. In certain embodiments, the oleanolic acid or a conjugate salt thereof is administered to the subject orally or intravenously.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens. In certain embodiments, the compounds described herein are administered to the subject on a once daily, once weekly, twice weekly, thrice weekly, once monthly, or twice monthly basis.

While the dosage will vary depending on the subject's age, body weight, symptom to be treated, desired therapeutic effect, administration route, term of treatment and the like, satisfactory effects can be obtained with the dosage of 0.001-1,000 mg/kg administered systemically in 1 to 5 divided doses a day or as a sustained form.

Disclosed herein is a new role of BAG3 in metabolic network, which was rarely reported before. Previous study in human hepatocellular carcinomas (HCC) cell lines found that, BAG3 was shown to directly interact with G6PD and inhibit the activity of G6PD. However, in patient and mice model which carry the BAG3 P209L mutation, the G6PD protein was decreased, suggest a novel role of BAG3 as the positive regulator of G6PD. G6PD is the rate-limiting enzyme of the pentose phosphate pathway (PPP), which is responsible for maintaining co-enzyme nicotinamide adenine dinucleotide phosphate (NADPH). PPP is also import for cellular defense to the oxidative stress. Without wishing to be bound by theory, the findings suggest that BAG3 may protect the cell from oxidative stress by regulating G6PD. The underlying molecular mechanism merits further investigation.

It is well known that X-linked genetic deficiency of G6PD causes non-immune hemolytic anemia and affects more than 400 million people worldwide. Recent studies have demonstrated that G6PD is involved in a number of neurological and neurodegenerative disorders, including amyotrophic lateral sclerosis (ALS), Huntington disease (HD), Parkinson disease (PD), Alzheimer Disease (AD). Based on the results disclosed herein deregulated G6PD is also implicated in Bag3opathy. Without wishing to be bound by theory, it is believed that G6PD could play a neuroprotective role in all these disorders. Decreased G6PD levels and impaired activities may lead to elevated reactive oxygen species (ROS) and oxidative damage. These findings also open an avenue to new therapeutics targeting G6PD for these disorders.

Oleanolic acid is known to be an activator of Nrf2. For the first time, it is demonstrated that oleanolic acid could increase G6PD through activation of Nrf2 in both mice and human. Oleanolic acid could be developed as a therapy for G6PD-deregulated disorders, such as Bag3opathy, ALS, HD, PD, and AD.

To verify that the plant extract containing oleanolic acid can also increase G6PD and improve the muscle dysfunction of Bag3opathy, in vivo studies in the BAG3 P209L/+ mice were performed with *Chaenomelis fructus* extract, which contained 27.18% oleanolic acid. The results demonstrated that *Chaenomelis fructus* extract can alleviate the contraction power decay of the posterior tibialis muscle and improve the ability to recover contractile force, indicating that *Chaenomelis fructus* extract has the potential to be developed as novel therapy for G6PD-deregulated disorders.

Experimental

Bag3opathy Patient and Healthy Controls

The Chinese patient was a 16-year-old girl (in the year of 2014) with diagnosis of MFM since 6 years old with gradual development of bilateral contracture of Achilles tendons. She conducted gene tests on Aug. 9, 2010 in Princess Margaret Hospital and mutation analysis with genomic DNA of the proband. Her muscle biopsy findings were suggestive of MFM on light microscopy and ultrastructural studies. Thirty healthy female subjects were recruited as control in accordance with the ethical principles of the Declaration of Helsinki, and obtained the consent form. Complete blood picture (CBP), fasting glucose, alanine transaminase (ALT), aspartate transaminase (AST), urea, creatinine, fasting triglycerides and total cholesterol were tested before the subjects participated in the study. The average age of study participants was 15.5 years old (SD: 8.80).

Metabolomics Analysis of the Serum

Serum Collection and Preparation

Serum was collected from patient and healthy volunteers, and immediately stored at −80° C. until analysis. The sample preparation procedures utilized standard methods for obtaining the metabolic profile of liquid biofluids. Briefly, for metabolite extraction, quadruple volumes of methanol/water (1:1 v/v) were added into samples, vortex-mixed for 30 s and centrifuged at 12,000 rpm for 10 min at 4° C. The supernatant was then transferred into new tubes with 10 μL of internal standard (IS, 0.1 mg mL$^{-1}$ of 4-chlorophenylalanine solution) for metabolomic analysis. Meanwhile, quality control samples for the analytical platform were prepared from a pooled mixture equally derived from all samples and preprocessed following steps as mentioned above.

UPLC/QTOF-MS Analysis

An ultrahigh-performance liquid chromatography system (UHPLC, Agilent 1290 Infinity, USA) was used for separation of endogenous metabolome through 1.7 μm BEH Amide column (2.1 mm×100 mm, Waters, USA). The mobile phase consisted of water with 0.1% formic acid (A) and acetonitrile containing 0.1% formic acid (B). The gradient program started from 90% B to 30% B in 12 min, 30% B kept for 1 min, and then returned to starting conditions in 0.1 min, re-equilibration until 18 min. A flow rate is 0.25 mL/min and constant temperature is 40° C. The separated components were subsequently fragmented and analyzed using a mass spectrometer. A quadrupole time-of-flight mass spectrometer (QTOF-MS, Agilent 6543, USA) was coupled with electrospray ionization source for fragmental collection. For full scan MS analysis, the QTOF-MS conditions were set as follows: the temperature for desolvation gas, 300° C.; gas flow, 8 L/min. The capillary voltage and cone voltage were set to 3.2 kV and 35 V for ESI+, and 3 kV and 50 V for ESI−, respectively. The mass range was set from 80 to 1000 m/z. The scan time was set at 0.3 s, and the inter scan delay was set at 0.02 s. The raw data were extracted and preprocessed by an XCMS software package based on R language (version 2.13.2) for baseline correction, smoothing, noise reduction, deconvolution, peak alignment and area calculation. The intensity of each metabolic signal was normalized by using internal standard. The p values for each fragment were calculated by t-type test and corrected with Benjamini-Hochberg false discovery rate (FDR) control procedure.

Metabolites Identification

Fragments with adjusted p value less than 0.1 were regarded as metabolic features. The target MS/MS acquisition mode was carried out, the MS/MS range was set from 30 to 800 m/z and the collision energies were set as 10 eV, 20 eV and 40 eV for comparing with chemical standards obtained from Sigma-Aldrich (St. Louis, MO, USA) or METLIN database. And other parameters under the target MS/MS acquisition mode were the same as settings in the full scan mode. Pathway analysis was done by MetaboAnalyst 3.0.

Determination of Serum Metabolites and Proteins with ELISA Kits

The concentration of G6P in serum was determined by High Sensitivity G6P Assay Kit (Catalog #: K687-100, BioVision, Inc. USA) following the manufacturer's instruction. Briefly, a volume of 200 μL of samples was deproteinized with 10 kDa MWCO spin filter prior to the reaction. After adding 50 μL of the appropriate reaction mix into each 50 μL of filtrate, the reaction was incubated for 5 min at 37° C. and protected from light. Finally, the concentration of G6P was calculated according the fluorescence intensity ($\lambda_{ex}$=535/$\lambda_{em}$=587) measured by fluorometer (EnVision 2104 Multilabel Reader, PerkinElmer, USA). The serum levels of G6PD (SEA716Hu, Cloud-Clone Corp), GPI, catalase (CAT), thioredoxin (TXN), and superoxide dismutase 1 (SOD1) were measured by Elisa Kits purchased from Cloud-Clone Crop Inc. (USA). Serum samples were diluted 100 folds in PBS for measurements of CAT and TXN, and were diluted 800 folds for SOD1 test. The activity of PGM was determined by Colorimetric Assay Kit from BioVision (Inc. USA). Samples were prepared and measured at 450 nm by Elisa reader (Benchmark Plus, BioRad, USA) depending on the manufacturer's instructions.

Establishment of BAG3 P209L Knock-In Mouse Model with CRISPR-Cas9

Creating $C_{57}BL/6$ mouse model with point mutation (P215L in mouse BAG3 gene) was performed by Cyagen Biosciences (Guangzhou, China) with CRISPR/Cas9-medited genome engineering. Equivalent mouse BAG3 protein mutation site was identified by sequence alignment between human- (UniProt ID: 095817) and mouse (UniProt ID: Q9JLV1) BAG3 protein sequence. The exon 3 of mouse BAG3 locus was selected as target site. Two gRNA targeting vectors and donor oligo sequences were designed. The vectors containing Cas9 mRNA and gRNA and donor oligo were co-injected into fertilized eggs for knock-in mouse production. Mutation site in donor oligo (P215L, CCC to CTC) was introduced into exon 3 of BAG3 locus by homology-directed repair. Mice pups were genotyped by PCR followed by sequence analysis.

Determination of G6PD in Mice Serum, Heart- and Skeletal Muscle (GZ)

BAG3 P209-KI mice were reproduced by mating between the P209L/+ male and female mice. All mice were maintained with free access to food and water in plastic cages at 22±2° C. and kept on a 12-h light/dark cycle. Animal welfare and experimental procedures were carried out in accordance with the related ethical regulations of Yunnan Minzu University. Eleven male BAG3 P209L-KI mice (4 WT, 4 P209L/+ and 3 P209L/P209L) of 16 months of age were sacrificed, and the blood were collected by enucleating the eyes and kept at room temperature for 2-3 h, then, it was centrifuged at 1,000 g for 20 min for serum separation. Heart muscle and skeletal muscle samples were obtained after cardiac perfusion with cold PBS. Muscle tissues were lysed into homogenate in ice-cold lysis buffer (150 mM NaCl, 50 mM Tris, pH7.5, 1% NP-40, 0.1% sodium deoxycholate) plus 1 mM PMSF. Samples were then sonicated on ice and centrifuged at 10,000 g for 5 min. The concentration of G6PD in serum, heart muscle, and skeletal muscle were determined by G6PD Elisa Kit (Catalog #: SEA716Mu, Cloud-Clone Corp. USA) following the manufacturer's instruction. The plate was read at 450 nm by the microplate reader (iMark, Biorad, USA). The concentration of the total protein from tissue samples was determined by the spectrophotometer (NanoDrop One, Thermo Scientific, USA).

Oleanolic Acid Treatment in Mice

Seventeen normal male $C_{57}BL/6$ mice, 6-8 weeks of age, were purchased from Hunan SJA Laboratory Animal Co., Ltd (Changsha, China). They were maintained with free access to food and water in plastic cages at 22±2° C. and kept on a 12-h light/dark cycle. Animal welfare and experimental procedures were carried out in accordance with the related ethical regulations of Yunnan Minzu University. Mice were randomly divided into one control group (n=6) and two dug treatment groups (n=5, 6). Oleanolic acid was suspended in 0.5% carboxymethylcellulose sodium (CMC-Na) solution with the concentration of 10 and 2.5 mg/mL. In the control and drug treatment groups, 0.5% CMC-Na and oleanolic acid (50, 200 mg/kg/day) was given orally for 10 days, respectively. On the $11^{th}$ day, mice were sacrificed, and the serum and tissue samples were prepared and detected as the method described previously.

Oleanolic Acid Treatment in Bag3opathy Patient

The Bag3opathy patient (body weight of patient: 40 kg) was orally administrated with Chinese medicine supplements containing oleanolic acid (180 mg per day) to evaluate the effects of treatment on BAG3 associated MFM for 3 months. 3 mL serum was collected for analysis before and after the treatment. The trial was approved the Ethics Committee of Hong Kong Baptist University (HASC/15-16/0268) according to the principles of the Declaration of Helsinki, and obtained the consent form.

*Chaenomelis fructus* Extract Preparation and Oleanolic Acid Content Determination Extraction and Purification of Oleanolic Acid from *Chaenomelis fructus*

Air-dried and powdered *Chaenomelis fructus* (5 g) was extracted with 150 mL of 95% ethanol under reflux at 75° C. for 2 h. The ethanol extract was then centrifuged at 3,900 r/min for 10 min. The supernatant was concentrated under reduced pressure at 50° C. using a rotary evaporator to remove ethanol. The resulting sticky residue was suspended in water and subjected to AB-8 macroporous resin column chromatography. Initially, the column was eluted with 5 BV of deionized water, then 5 BV of 50% ethanol was used to remove the high polar impurities. Finally, column was eluted with 5 BV of 75% ethanol to obtain the oleanolic acid-rich fraction, which was further concentrated under reduced pressure at 50° C. using a rotary evaporator to yield oleanolic acid-rich extract.

HPLC Analysis of Oleanolic Acid from *Chaenomelis fructus*

The *Chaenomelis fructus* extract was analyzed using an Agilent 1290 Infinity II LC system (Agilent, Pal Alto, CA, USA), and separated with an Alltima $C_{18}$ column (250 mm×4.6 mm, 5 Ilm). The mobile phase was comprised of solvent A (acetic acid:triethylamine:$H_2O$=0.30:0.15:900) and solvent B (acetic acid:triethylamine:methanol=0.30: 0.15:900) with isocratic elution: 0-40 min, 90% B. The total flow rate was 0.8 mL/min. Analyses were carried out at room temperature and the detection wavelength was set at 210 nm.

*Chaenomelis fructus* Extract Treatment in Mice

BAG3 P209L/+ mice (32 weeks old) were randomly divided into 3 groups, with 5 mice in each group (Control group, *Chaenomelis fructus* extract 150 mg/kg/day, *Chaenomelis fructus* extract 300 mg/kg/day). The mice were maintained with free access to food and water in plastic cages at 22±2° C. and kept on a 12-h light/dark cycle.

To investigate the contractility of the skeletal muscles of the rear appendages of BAG3 P209L/+ mice under physiological conditions, the mice were temporarily unconscious by respiratory anesthesia, and the body temperature was maintained using a warming lamp. The hindlimb used for testing was stabilized with cloth tape on the knee and foot. Muscles were stimulated by needle electrodes inserted beneath the skin through electrical stimulation to induce the contraction of the posterior tibialis muscle.

Four sub-groups of multi-cycle low-frequency tetanic contraction were performed during 12 days as a skeletal muscle exercise training protocol, each an interval of 4 days, and the fatigue trend of the 4 groups of the low-frequency tetanic contraction peak was analyzed comparatively. The protocol adopted a stimulation frequency of 40 Hz to repeatedly contract skeletal muscle 80 times, each stimulation of 1,000 ms, with a rest interval of 2,000 ms.

Statistical Methods

Comparing two groups of biological samples is frequently seen in biomedical research. In terms of the measurements following normal distribution, T-statistic is usually used to test the difference between two groups (Eq.1).

$$T = \frac{\overline{X_1} - \overline{X_2}}{\sqrt{s_1^2/n_1 + s_2^2/n_2}} \quad \text{(Eq. 1)}$$

Where $\overline{X_1}$ is the mean value of measurement on first group, while $\overline{X_2}$ is the mean value of measurement on second group. $s_1^2$ is the sample variance of first group, and $s_2^2$ is the sample variance of second group. Whereas $n_1$ and $n_2$ are the number of biological replicates in first and second group, respectively. The Bag3opathy cases are extremely rare and only one Chinese patient can be found for us. Therefore, the disease group (first group) has one biological replicate ($n_1$=1), while the healthy control group (second group) has 30 biological replicates ($n_2$=30). The key problem is that, without biological replicates, the sample variance of disease group can't be calculated directly. Even so, an alternative way to estimate $s_1^2$ is to "borrow" sample variance from the healthy control group, making $s_1^2$ equals to $s_2^2$. This leads to the following statistic.

$$T' = \frac{\overline{X_1} - \overline{X_2}}{\sqrt{s_2^2(1 + 1/n_2)}} \quad \text{(Eq. 2)}$$

T'-statistic follows the exact t-distribution with $n_2-1$ degrees of freedom. This approach, namely t-type test, was used for comparing the single patient with multiple healthy controls.

Results

Clinical Manifestations of Bag3opathy Patient

The girl had a history of restrictive lung disease previously diagnosed as asthma. She progressed rapidly with proximal myopathy, rigid spine, and bilateral tightening of the Achilles tendons requiring surgical elongation. Hypertrophic cardiomyopathy with restrictive physiology was shown by echocardiogram. Moreover, prolonged QT interval was also noted in the patient. Family history was unremarkable yet her father was incidentally found to have prolonged QT interval. She was found to have mild proximal muscle weakness of both legs and later both arms, both of Medical Research Council Grade 4. Nerve conduction study showed decreased motor (tibial and peroneal) amplitudes (0.3/0.7 mV; 0.4/0.5 mV) and latencies (29/33 m/s; 28.7/34.3 m/s). She had been using a wheelchair for about one and half year 70-80% of time and found diminished lower limb strength. Her lung function test showed moderate restrictive pattern and need to use BiPAP nightly. Her appetite was good and had regular menstruation cycles.

Previously, mutation analysis showed that this girl is a carrier of heterozygous BAG3 gene with de novo mutation c.626C>T (p.Pro209Leu, P209L) and a germline variation c.772C>T (p.Arg258Trp). The levels of eosinophil and platelet of this girl were lower than normal. Using biochemical assay, a 6-fold elevation of creatine kinase (CK) and normal blood glucose was found. The total cholesterol, including HDL-, LDL cholesterol, and triglycerides, were also lower than normal levels (Table 1). To further investigate the global perturbations induced by mutant BAG3 in this girl, a serum metabolomics study was carried out for systematic analysis of her serum sample compared to 30 healthy matched girls.

TABLE 1

Patient characteristics

| | Item | Value | Reference value |
|---|---|---|---|
| General | Gender | Female | NA |
| | Age | 16 | NA |
| Blood test | Eosinophils (%) | 4.2 | 0.0-3.4 |
| | Platelet count (K/μL) | 183 | 193-345 |
| Biochemistry assay | Glucose (mM/L) | 5.1 | <5.6 |
| | Creatine kinase (IU/L) | 953 | <154 |
| | Total cholesterol (mM/L) | 4.00 | 5.17-6.18 |
| | HDL cholesterol (mM/L) | 1.40 | >1.53 |
| | LDL cholesterol (mM/L) | 2.22 | 2.59-3.34 |
| | Triglycerides (mM/L) | 0.83 | 1.69-2.25 |

Figure 2:
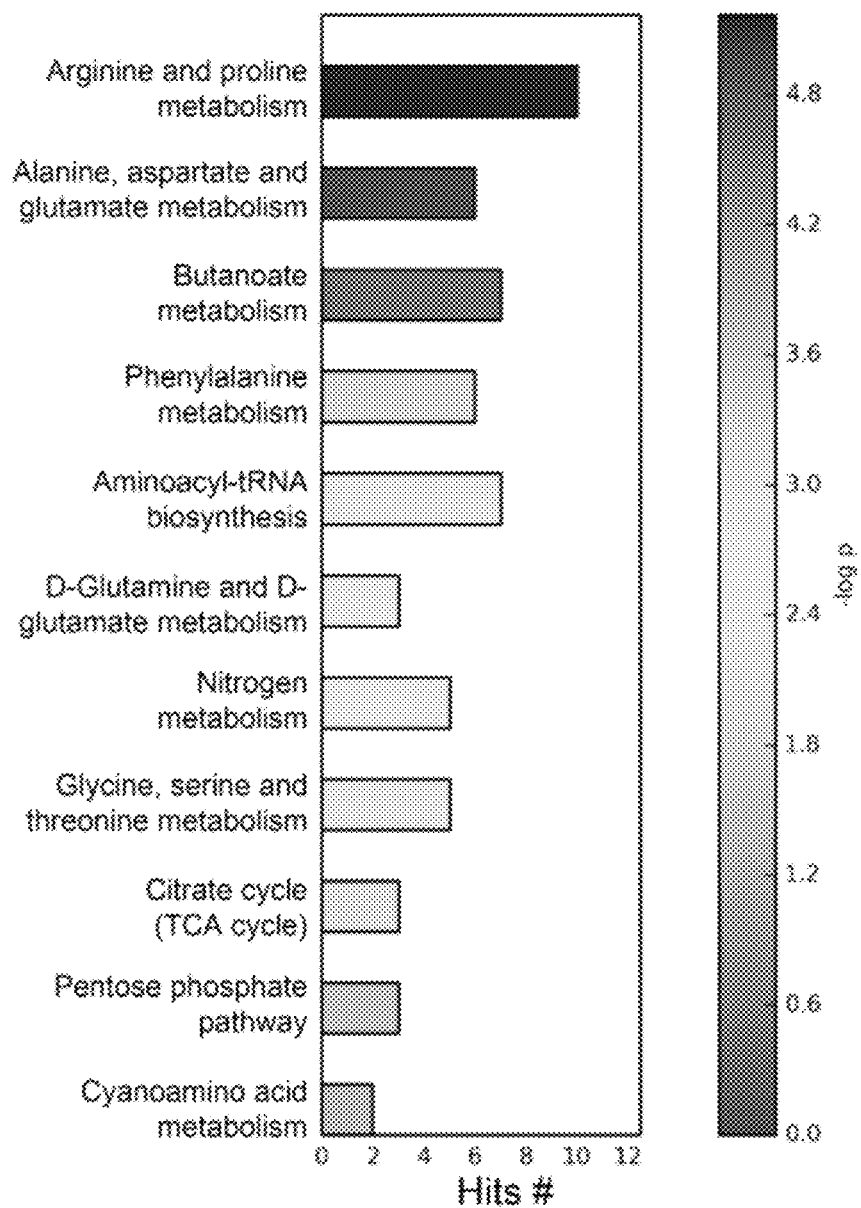
FIG. 2 shows serum metabolome analysis of Bag3opathy patient. Metabolic pathways overrepresented by significantly altered metabolites.

Serum Metabolomics Analysis Identified Aberrant High Level of G6P and Low Level of G6PD Ultrahigh performance liquid chromatography coupled with high resolution mass spectrometry was used to profile the small molecule metabolites in serum of Bag3opathy patient. The patient and healthy controls were well separated by principal component analysis (PCA), either with negative mode features or in positive mode features. More than 100 metabolites were identified in both modes. The t-type test conjunction with FDR control was used to probe the significance of differences between single patient and a group of healthy controls. As a result, a total of 64 metabolites with significant alterations (adjusted p value <0.3) were selected (FIG. 1 and Table 2). Pathway analysis suggested overrepresented pathways in amino acid metabolism and glucose metabolism (FIG. 2 and Table 3).

TABLE 2

Significantly changed metabolites in Bag3opathy patient

| Metabolite | Mode | RT | m/z | Mass | Fold Change (log2) | P-value (t-type test) | Adjusted P-Value |
|---|---|---|---|---|---|---|---|
| trans-Cinnamic acid | pos | 5.55 | 149.06 | 148.06 | −3.10 | 0.00 | 0.00 |
| Tetrahydrocortisone | pos | 1.29 | 365.23 | 364.22 | −2.52 | 0.06 | 0.21 |
| Glycoursodeoxycholic acid | pos | 1.73 | 450.32 | 449.31 | −2.38 | 0.08 | 0.23 |
| Butyric acid | pos | 1.32 | 89.06 | 88.05 | −2.22 | 0.01 | 0.08 |
| Cortisol 21-acetate | pos | 1.33 | 405.22 | 404.21 | −2.16 | 0.00 | 0.00 |
| Sucrose | neg | 7.02 | 341.11 | 342.12 | −2.14 | 0.07 | 0.27 |
| Equol | pos | 7.52 | 243.11 | 242.10 | −1.96 | 0.00 | 0.02 |
| Creatinine | pos | 2.55 | 114.07 | 113.06 | −1.92 | 0.00 | 0.02 |
| L-Malic acid | neg | 2.53 | 133.01 | 134.02 | −1.86 | 0.02 | 0.15 |

TABLE 2-continued

Significantly changed metabolites in Bag3opathy patient

| Metabolite | Mode | RT | m/z | Mass | Fold Change (log2) | P-value (t-type test) | Adjusted P-Value |
|---|---|---|---|---|---|---|---|
| Gamma aminobutryic acid | neg | 5.61 | 102.06 | 103.06 | −1.81 | 0.04 | 0.20 |
| Glyceric acid | neg | 2.55 | 105.02 | 106.03 | −1.60 | 0.00 | 0.01 |
| L-Glutamate | pos/neg | 5.53 | 148.06 | 147.05 | −1.54 | 0.00 | 0.00 |
| Betaine | neg | 5.00 | 116.07 | 117.08 | −1.53 | 0.02 | 0.12 |
| 4-Pyridoxic acid | neg | 4.99 | 182.04 | 183.05 | −1.50 | 0.04 | 0.20 |
| 3-Hydroxyvalproic acid | neg | 1.31 | 159.10 | 160.11 | −1.42 | 0.00 | 0.04 |
| Propionylcarnitine | pos | 1.70 | 218.14 | 217.13 | −1.41 | 0.01 | 0.08 |
| L-Aspartic Acid | pos/neg | 5.99 | 134.04 | 133.04 | −1.39 | 0.01 | 0.06 |
| Sphingosine-1-phosphate | pos | 1.31 | 380.26 | 379.25 | −1.33 | 0.05 | 0.19 |
| Cytidine | neg | 6.83 | 242.08 | 243.09 | −1.30 | 0.01 | 0.06 |
| Fumaric acid | neg | 2.53 | 115.00 | 116.01 | −1.29 | 0.02 | 0.13 |
| 3-Methyl-L-histidine | pos | 6.74 | 170.09 | 169.08 | −1.21 | 0.01 | 0.05 |
| Butyryl-L-carnitine | pos | 1.66 | 232.15 | 231.15 | −1.10 | 0.03 | 0.15 |
| Acetylcholine | pos | 1.56 | 146.12 | 145.11 | −1.02 | 0.02 | 0.11 |
| L-Erythrulose | neg | 2.50 | 119.03 | 120.04 | −1.02 | 0.08 | 0.29 |
| Cortolone | pos | 1.30 | 367.24 | 366.23 | −0.86 | 0.06 | 0.20 |
| L-Proline | pos/neg | 7.32 | 116.07 | 115.06 | −0.85 | 0.00 | 0.03 |
| 2-Hydroxyglutarate | neg | 2.14 | 147.03 | 148.04 | −0.80 | 0.06 | 0.25 |
| L-Ornithine | pos | 7.31 | 133.10 | 132.09 | −0.78 | 0.00 | 0.04 |
| Gluconic acid | neg | 5.62 | 195.05 | 196.06 | −0.73 | 0.07 | 0.26 |
| Citrulline | pos | 6.29 | 176.10 | 175.10 | −0.64 | 0.10 | 0.27 |
| p-Coumaric acid | pos | 5.22 | 165.05 | 164.05 | −0.64 | 0.03 | 0.15 |
| Indoleacetaldehyde | pos | 6.29 | 160.08 | 159.07 | −0.59 | 0.10 | 0.26 |
| 2-Pyrrolidone-5-carboxylic acid | neg | 2.13 | 128.04 | 129.04 | −0.58 | 0.02 | 0.12 |
| L-Phenylalanine | pos | 4.00 | 166.09 | 165.08 | −0.47 | 0.10 | 0.26 |
| Succinic acid | neg | 2.53 | 117.02 | 118.03 | −0.45 | 0.05 | 0.22 |
| L-Leucine | pos | 3.85 | 132.10 | 131.09 | −0.39 | 0.07 | 0.21 |
| L-Tryptophan | pos/neg | 3.98 | 205.10 | 204.09 | −0.39 | 0.04 | 0.16 |
| Vitamin D3 | pos | 15.39 | 385.35 | 384.34 | 0.16 | 0.11 | 0.29 |
| Palmitic acid | pos | 15.39 | 257.25 | 256.24 | 0.17 | 0.10 | 0.27 |
| L-Glutamine | neg | 6.13 | 145.06 | 146.07 | 0.27 | 0.04 | 0.20 |
| L-Fucose | pos | 1.77 | 165.08 | 164.07 | 0.49 | 0.09 | 0.26 |
| 3-Methyl-2-oxovaleric acid | neg | 1.33 | 129.06 | 130.06 | 0.52 | 0.04 | 0.20 |
| Chenodeoxycholic acid 3-sulfate | pos | 1.25 | 473.27 | 472.26 | 0.54 | 0.02 | 0.09 |
| Alpha-ketoisovaleric acid | neg | 1.42 | 115.04 | 116.05 | 0.64 | 0.00 | 0.01 |
| Acetylcarnitine | pos | 1.81 | 204.12 | 203.12 | 0.84 | 0.02 | 0.11 |
| (−)-Epinephrine | pos | 2.32 | 184.09 | 183.09 | 0.94 | 0.00 | 0.00 |
| Cytidine diphosphate choline | pos | 3.15 | 489.12 | 488.11 | 1.00 | 0.01 | 0.09 |
| Trigonellinamide | pos | 3.02 | 137.07 | 136.06 | 1.07 | 0.03 | 0.13 |
| Stearic acid | pos | 1.40 | 285.28 | 284.28 | 1.13 | 0.06 | 0.21 |
| Isovaleric acid | neg | 1.33 | 101.06 | 102.07 | 1.13 | 0.00 | 0.00 |
| Palmitoyl Ethanolamide | pos | 1.71 | 300.29 | 299.28 | 1.13 | 0.00 | 0.00 |
| Hydroquinone | neg | 1.61 | 109.03 | 110.04 | 1.21 | 0.01 | 0.07 |
| Alanine | pos/neg | 5.44 | 90.06 | 89.05 | 1.33 | 0.00 | 0.00 |
| Palmitic amide | pos | 1.31 | 256.26 | 255.26 | 1.37 | 0.01 | 0.07 |
| 13Z-Docosenamide | pos | 1.55 | 338.34 | 337.33 | 1.39 | 0.06 | 0.20 |
| Creatine | pos/neg | 5.44 | 132.08 | 131.07 | 1.39 | 0.00 | 0.00 |
| Oleamide | pos | 1.31 | 282.28 | 281.27 | 1.44 | 0.01 | 0.09 |
| Glycerophosphocholine | neg/pos | 1.36 | 256.09 | 257.10 | 1.51 | 0.00 | 0.01 |
| Cytosine | neg | 1.61 | 110.03 | 111.04 | 1.61 | 0.01 | 0.09 |
| Pyridoxal | pos | 5.50 | 168.06 | 167.06 | 1.63 | 0.05 | 0.19 |
| Cytidine diphosphate | neg | 5.42 | 402.01 | 403.02 | 1.69 | 0.00 | 0.00 |
| 3-Hydroxybutyric acid | neg | 1.40 | 103.04 | 104.05 | 2.28 | 0.00 | 0.00 |
| D-myo-Inositol-1,3,4,5-tetraphosphate | neg | 1.27 | 498.93 | 499.94 | 2.74 | 0.00 | 0.00 |
| Glucose 6-phosphate | neg | 1.51 | 259.03 | 260.04 | 4.88 | 0.00 | 0.00 |

TABLE 3

Metabolic pathways overrepresented by significantly changed metabolites in Bag3opathy patient

| No. | Metabolic pathway | Hits # | P-value | Altered metabolites |
|---|---|---|---|---|
| 1 | Arginine and proline metabolism | 10 | 6.74E−06 | L-Glutamine; L-Glutamic acid; Citrulline; L-Aspartic acid; Fumaric acid; Ornithine; L-Proline; Creatine; Creatinine; Gamma-Aminobutyric acid |
| 2 | Alanine, aspartate and glutamate metabolism | 6 | 1.18E−05 | L-Glutamine; L-Glutamic acid; Gamma-Aminobutyric acid; Succinic acid; L-Aspartic acid; Fumaric acid |
| 3 | Butanoate metabolism | 7 | 2.59E−05 | L-Glutamic acid; Gamma-Aminobutyric acid; Succinic acid; Fumaric acid; 2-Hydroxyglutarate; Butyric acid; 3-Hydroxybutyric acid |
| 4 | Phenylalanine metabolism | 5 | 4.88E−04 | L-Phenylalanine; trans-Cinnamic acid; 4-Hydroxycinnamic acid(p-Coumaric acid); Fumaric acid; Succinic acid |
| 5 | Aminoacyl-tRNA biosynthesis | 7 | 1.46E−03 | L-Phenylalanine; L-Aspartic acid; L-Glutamine; L-Glutamic acid; L-Leucine; L-Tryptophan |
| 6 | D-Glutamine and D-glutamate metabolism | 3 | 1.73E−03 | L-Glutamine; L-Glutamic acid; Pyrrolidonecarboxylic acid |
| 7 | Nitrogen metabolism | 5 | 1.79E−03 | L-Phenylalanine; L-Tryptophan; L-Glutamine; L-Glutamic acid; L-Aspartic acid |
| 8 | Glycine, serine and threonine metabolism | 5 | 4.54E−03 | L-Aspartic acid; Glyceric acid; L-Tryptophan; Creatine; Betaine |
| 9 | Citrate cycle (TCA cycle) | 3 | 1.03E−02 | L-Malic acid; Succinic acid; Fumaric acid |
| 10 | Pentose phosphate pathway | 3 | 3.67E−02 | G6P; Gluconic acid; Glyceric acid |
| 11 | Cyanoamino acid metabolism | 2 | 5.18E−02 | Alanine; L-Aspartic acid |

Figure 3:
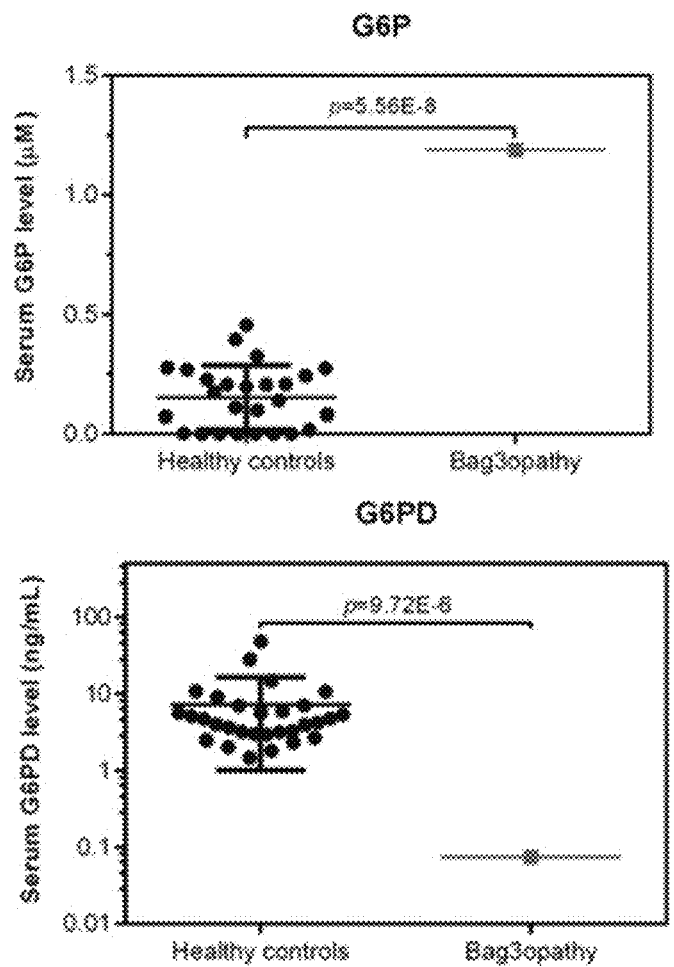
FIG. 3 shows the levels of glucose-6-phosphate (G6P) and major transformation enzyme in Bag3opathy patient and healthy controls determined by ELISA Kit. G6PD; GPI, glucose-6-phosphate isomerase (GPI), and phophoglucomutase (PGM).
Figure 3:
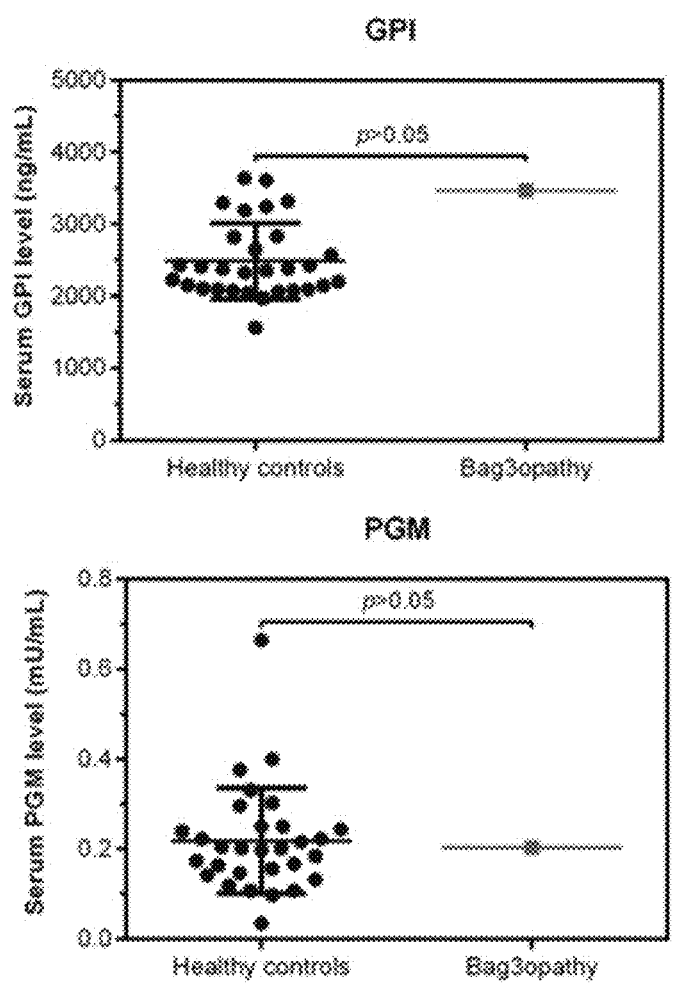

The most striking finding was that glucose-6-phophate (G6P), was dramatically increased (log 2 fc=4.88, adjusted p value <0.01) in Bag3opathy patient. Consistently, serum G6P level of BAG3opathy patient determined by ELISA kits was 1.19 µM, significantly higher (p value=5.56E-8) than that of healthy controls (0.15±0.13 µM) (FIG. 3). Since the abnormally elevated G6P could be due to the deregulation of several G6P-related enzymes, the inventors also determined the serum levels/activities of three major G6P transformation enzymes: G6PD, GPI, and PGM. As anticipated, the serum G6PD of Bag3opathy patient was almost diminished (0.07 ng/mL), and significantly lower (−99.0%, p value=9.72E-6) than the normal level (7.25±9.38 ng/mL) (FIG. 3). Meanwhile, the serum level of GPI and activity of PGM showed no difference between Bag3opathy patient and healthy controls (FIG. 3). These findings suggested aberrant low level of G6PD enzymes occurs in Bag3opathy patient. However, whether mutation in BAG3 causes decreased G6PD is still unclear. To test such hypothesis, we set out to establish a Bag3opathy mice model.

P209L Knock-In Mice Exhibited Muscle Weakness and Decreased G6PD

Previous work has reported that knock-out (KO) of Bag3 in mice resulted in severe muscle dysfunction and early lethality, or induced aggravated diabetic nephropathy. Recently, a transgenic (TG) mouse model with cardiomyocyte-specifically expressed human BAG3 P209L has been reported. To some extent, these KO or TG mouse models are similar, but not close to, the case of the Bag3opathy patient. Thus, a knock-in (KI) mouse model was esbtalished, which carries the equivalent disease mutation in mice BAG3 gene.

Figure 5:
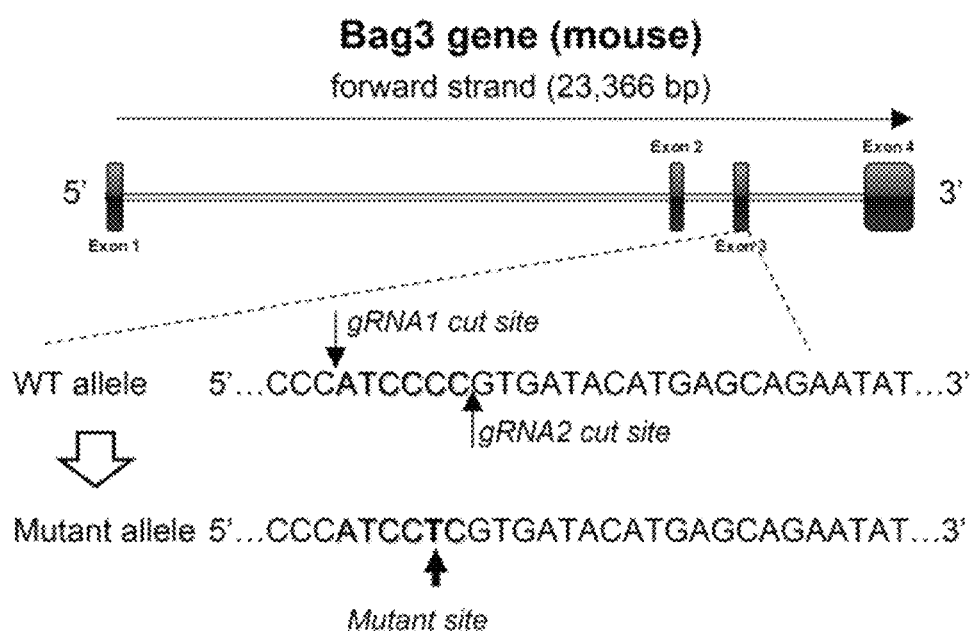
FIG. 5 shows the genome editing at mouse Bag3 locus by CRISPR/Cas9. The schematic depiction of mouse Bag3 locus was presented. The exons were colored in dark, while the introns were colored in grey. The editing sites were in the third exon. The cut sites of guide RNA (gRNA) were shown in thin arrow, and mutated nucleotide was highlighted by bold arrow (SEQ ID NO: 5 and SEQ ID NO: 6).

To identify the mutation site, the human BAG3 protein sequence (UniProt ID: O95817) was aligned with mouse BAG3 protein sequence (UniProt ID: Q9JLV1). The conserved 'IPV' motif was found in mouse BAG3 protein (FIG. 4), suggesting conserved biological functions may be mediated by the 'IPV' motif among human and mouse. From the sequence comparison, it can be inferred that the disease-causing mutation in mouse BAG3 would be P215L (FIG. 4), which is encoded by $exon_3$ in mouse BAG3 gene locus (FIG. 5, Table 4). The guide RNA (gRNA) and donor oligo sequences were carefully designed (FIG. 5), and the single mutation (CCC to CTC) at mouse Bag3 gene was introduced by CRISPR-Cas9 mediated genome editing and homology-directed repair (FIG. 5). Born mice pups were genotyped by PCR and DNA sequencing (Table 5).

TABLE 4

The structure of mouse Bag3 locus (Chromosome 7)

| Exon/Intron | Start | End | Length |
|---|---|---|---|
| Exon 1 | 128523616 | 128524044 | 429 |
| Intron 1-2 | 128524045 | 128539972 | 15928 |
| Exon 2 | 128539973 | 128540311 | 339 |
| Intron 2-3 | 128540312 | 128541806 | 1495 |
| Exon 3 | 128541807 | 128542208 | 402 |
| Intron 3-4 | 128542209 | 128545589 | 3381 |
| Exon 4 | 128545590 | 128546981 | 1392 |

TABLE 5

The primers for PCR genotyping of Bag3opathy mouse model by DNA sequencing

| | |
|---|---|
| Mouse Bag3-F | 5'-GGAGTGGTGCTGGAGATTGAAACC-3' (Gene ID: 29810; SEQ ID NO: 7) |
| Mouse Bag3-R | 5'-GAAGCACCTCTGACGGGTGACCT-3' (Gene ID: 29810; SEQ ID NO: 8) |
| Product size | 506 bp |
| Annealing temperature | 60° C. |

Figure 6:
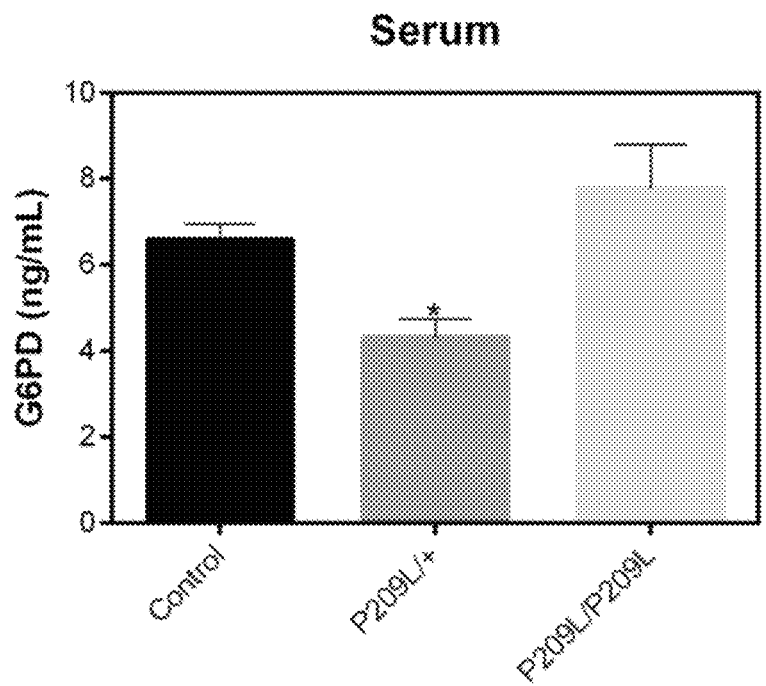
FIG. 6 shows the G6PD levels in the serum samples of P209-KI mice (Control: n=4; P209L/+: n=4; P209L/P209L: n=3). *, p<0.05.
Figure 7:
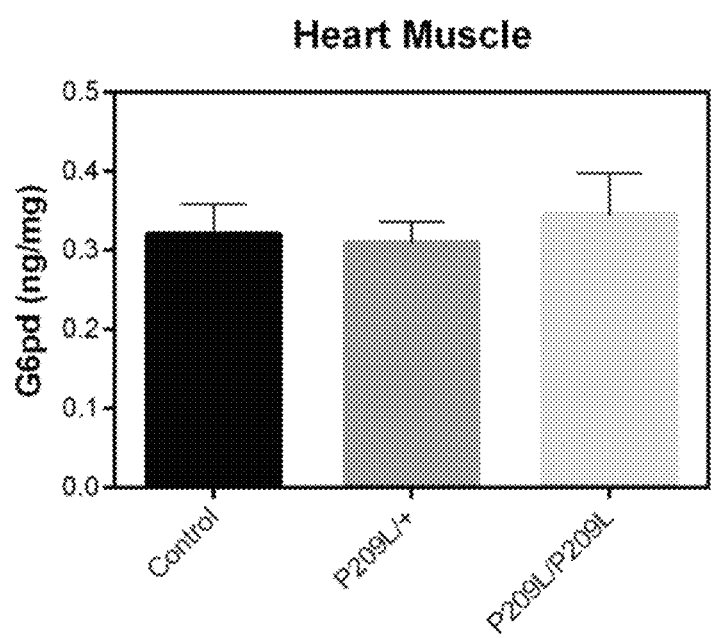
FIG. 7 shows the G6PD levels in the heart muscle samples of P209-KI mice (Control: n=4; P209L/+: n=4; P209L/P209L: n=3).
Figure 8:
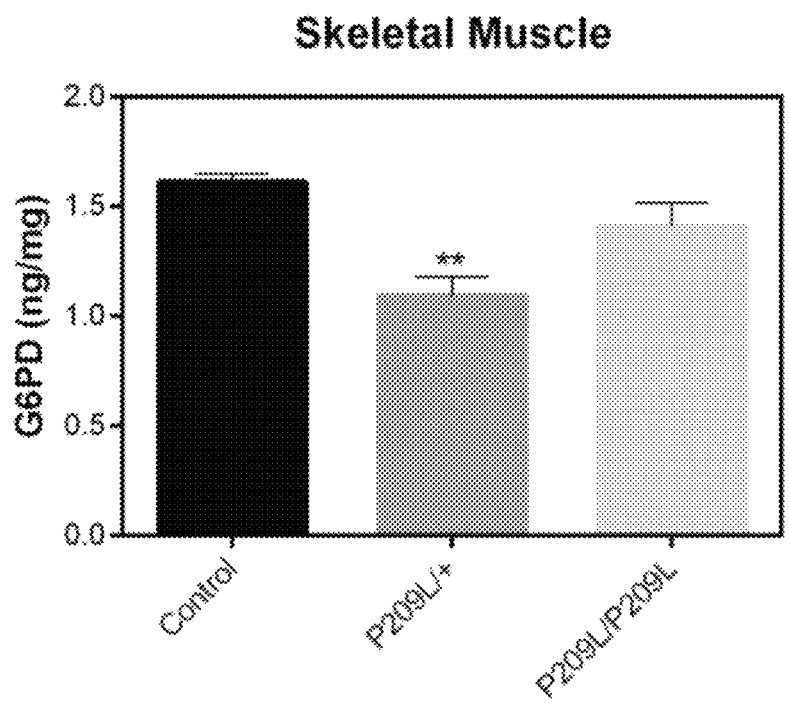
FIG. 8 shows the G6PD levels in the skeletal muscle samples of P209-KI mice (Control: n=4; P209L/+: n=4; P209L/P209L: n=3). **, p<0.01.

Two female heterogeneous P209L-KI mice (P209L/+) were observed with weak hind legs, suggesting that the KI mouse models could develop muscle weakness like phenotype observed in the human Bag3opathy patient. Meanwhile, the level of mouse G6PD were determined by ELISA kit. Consistently, the G6PD protein was significantly decreased in the heterogeneous, but not homogeneous, in the serum (4.29±0.87 ng/mL, n=4) and skeletal muscle (1.09±0.17 ng/mg, n=4) samples of P209L KI mice, compared with that of wild type (6.57±0.73 ng/mL and 1.61±0.08 ng/mg, in serum and skeletal muscle respectively, n=4) (FIG. 6 and FIG. 8). No difference of G6PD was detected in the heart muscle (FIG. 7). These results suggested that BAG3 P209L mutation causes muscle weakness and decreased G6PD in the mice model.

Figure 9:
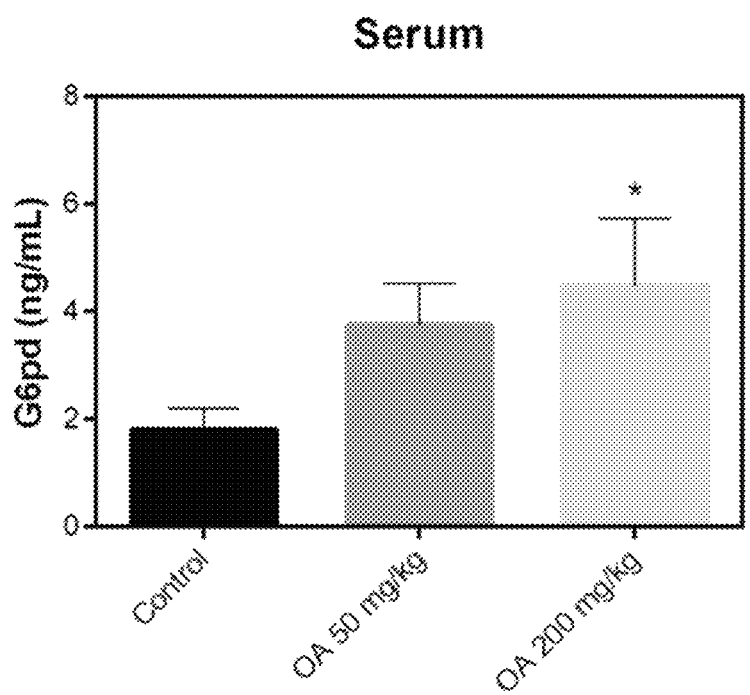
FIG. 9 shows the change of G6PD protein in serum of normal mice orally administrated with oleanolic acid (50 mg/kg and 200 mg/kg) for 10 days. *, p<0.05.
Figure 10:
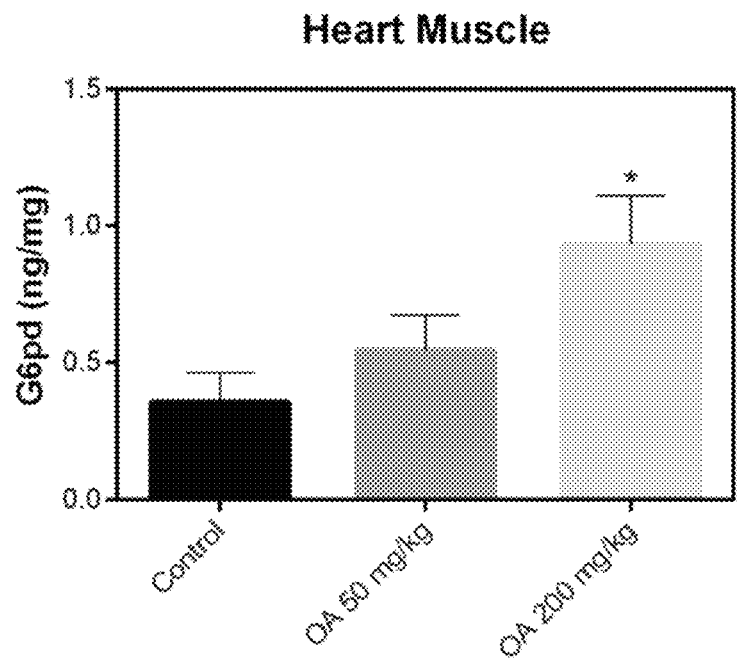
FIG. 10 shows the change of G6PD protein in heart muscle of normal mice orally administrated with oleanolic acid (50 mg/kg and 200 mg/kg) for 10 days. *, p<0.05.
Figure 11:
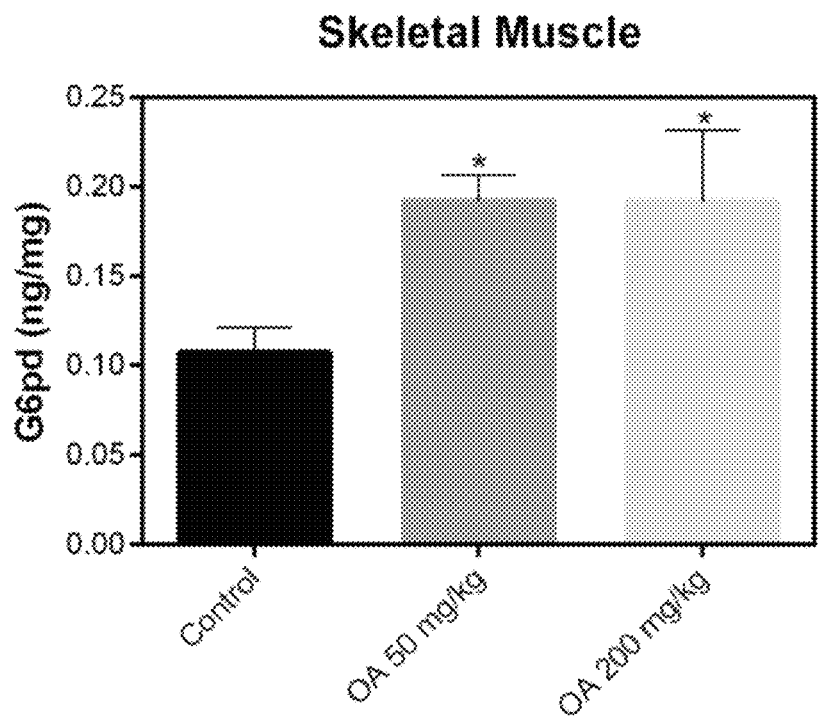
FIG. 11 shows the change of G6PD protein in skeletal muscle of normal mice orally administrated with oleanolic acid (50 mg/kg and 200 mg/kg) for 10 days. *, p<0.05.

Oral Administration of Oleanolic Acid Increased G6PD in Serum, Heart- and Skeletal Muscle in Mice Daily oral administration of oleanolic acid (50 and 200 mg/kg) for ten days in normal mice resulted in significant increases in G6PD protein levels in serum samples were significantly increased (FIG. 9): control group (n=6), 1.79±0.99 ng/mL; oleanolic acid 50 mg/kg group (n=6), 3.74±1.91 ng/mL (p=0.140); oleanolic acid 200 mg/kg group (n=6), 4.47±3.07 ng/mL (p=0.049). The G6PD protein was also increased in heart muscle (FIG. 10): control group (n=6), 0.36±0.26 ng/mg; oleanolic acid 50 mg/kg group (n=6), 0.54±0.32 ng/mg (p=0.36); oleanolic acid 200 mg/kg group (n=6), 0.93±0.43 ng/mg (p=0.011). Similar changes of G6pd were also observed in skeletal muscle (FIG. 11): control group (n=6), 0.11±0.04 ng/mg; oleanolic acid 50 mg/kg group (n=6), 0.19±0.04 ng/mg (p=0.035); oleanolic acid 200 mg/kg group (n=6), 0.19±0.10 ng/mL (p=0.035). Taken together, oral administration of oleanolic acid increased G6PD protein concentration in serum, heart muscle, and skeletal muscle of normal mice.

Figure 12:
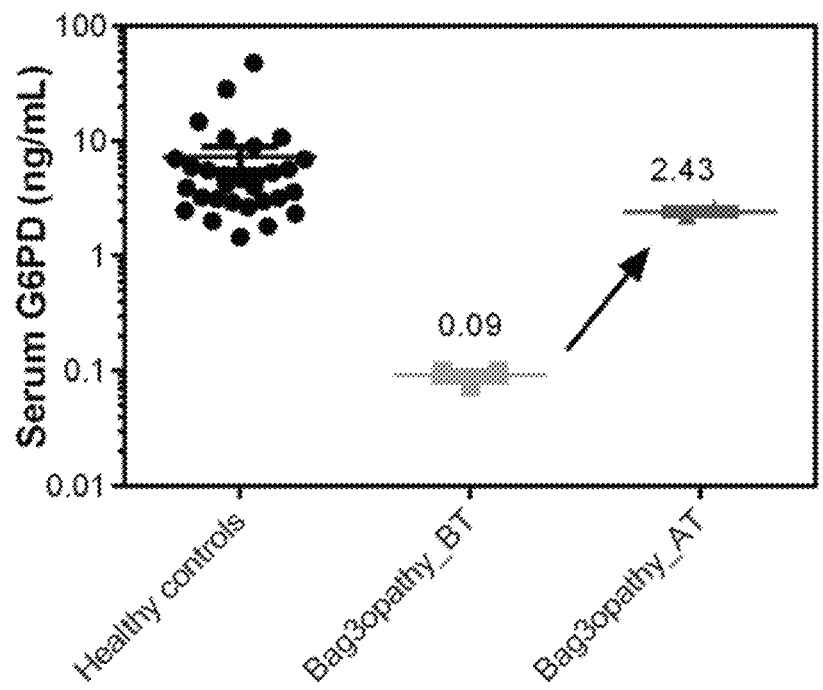
FIG. 12 shows the change of G6PD protein in Bag3opathy patient orally administrated oleanolic acid capsule (180 mg/day) for three months.
Figure 13:
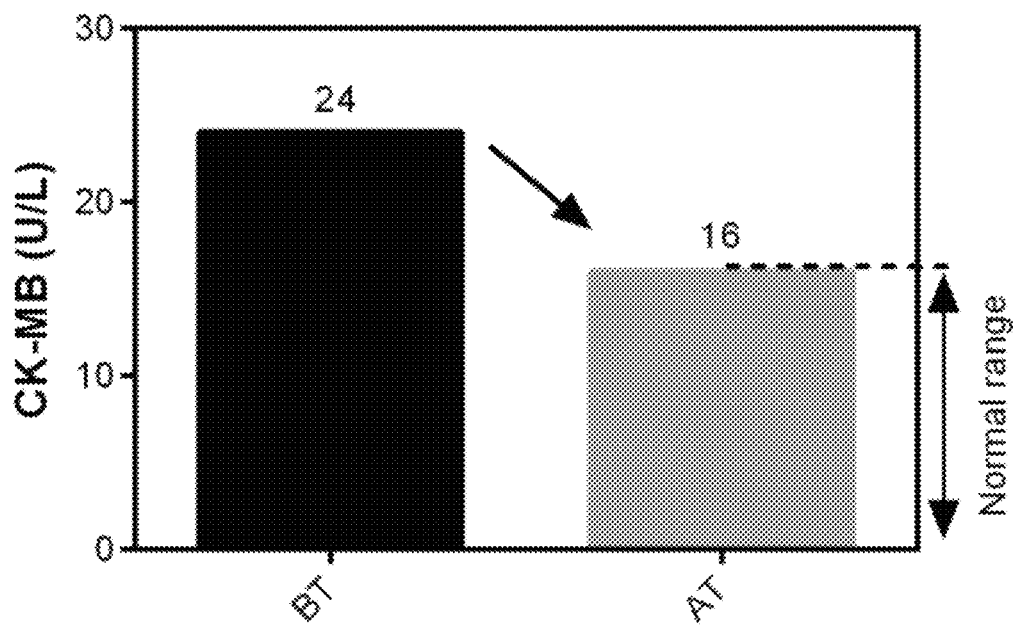
FIG. 13 shows the change of CK-MB in Bag3opathy patient orally administrated with oleanolic acid capsule (180 mg/day) for three months.

Oleanolic Acid Treatment Increased Serum G6PD and Improved Heart Function in Bag3opathy Patient With the G6PD increasing effect, it was possible that the Bag3opathy patient could benefit from oleanolic acid treatment. With carefully designed protocol, the 18-year girl took oleanolic acid capsules (180 mg/day) for three months. Consistently, the serum G6PD protein was significantly increased, from 0.09 ng/mL to 2.43 ng/mL, which was closer to the average level of normal girls (7.25±9.38 ng/mL) (FIG. 12). Surprisingly, creatine kinase-MB (CK-MB), a cardiac marker in subject's blood, was dramatically attenuated: before treatment, 24 U/L; after treatment, 16 U/L (FIG. 13). These results suggested that oral administration of oleanolic acid could increase G6PD and improve the heart function in this Bag3opathy patient.

Figure 14:
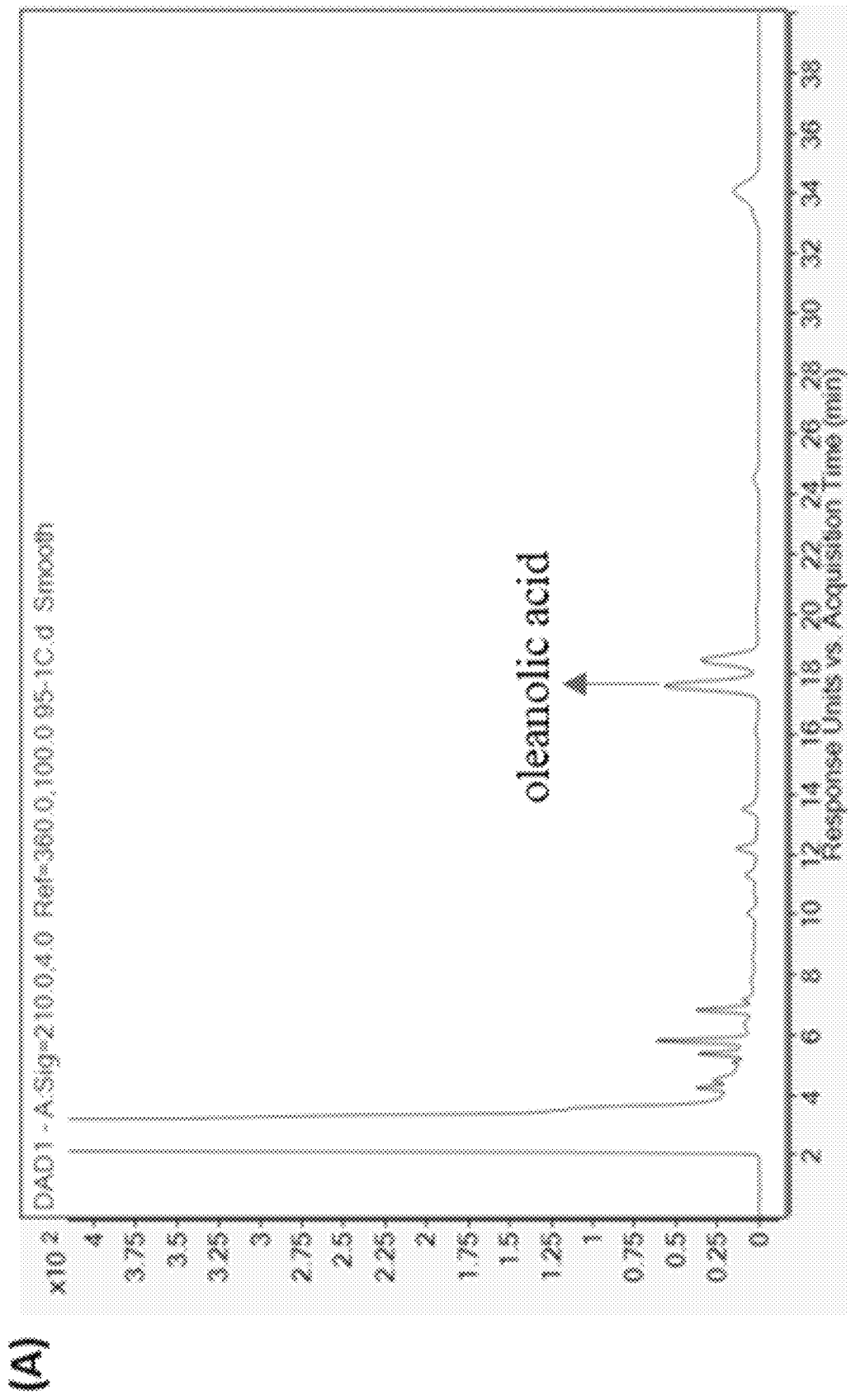
FIG. 14 shows the HPLC chromatogram of oleanolic acid from *Chaenomelis fructus* extract before (A) and after (B) purification using AB-8 resin column chromatography.
Figure 14:
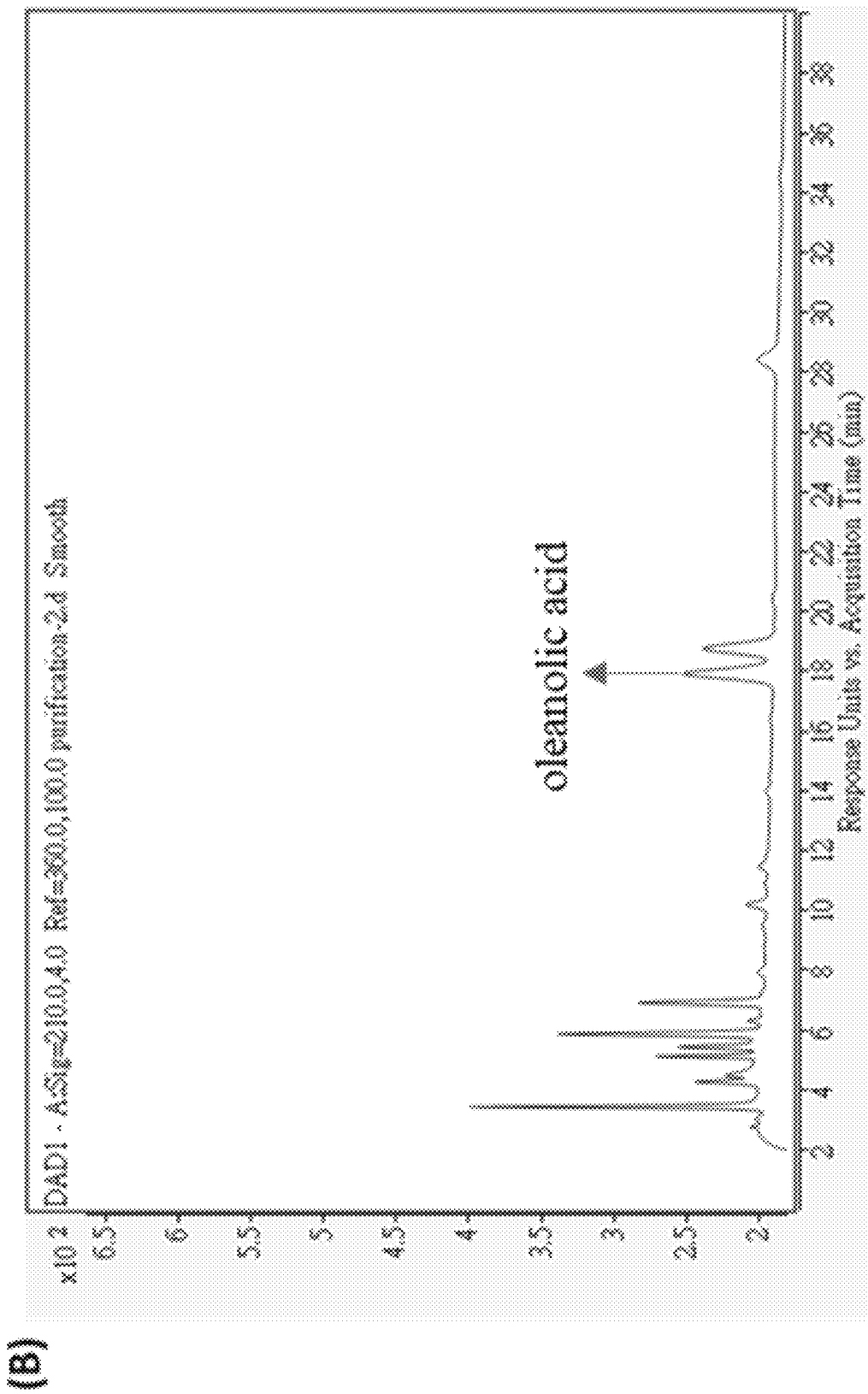

Oral Administration of *Chaenomelis fructus* Extract Improve the Muscle Dysfunction in P209L-KI Mouse Model HPLC chromatogram of oleanolic acid from *Chaenomelis fructus* extract before and after purification were shown in FIG. 14. The content of oleanolic acid in the *Chaenomelis fructus* extract was 0.33%, and after the purification using AB-8 resin column chromatography, the content of oleanolic acid in the extract increased from 1.87% to 27.18%.

Figure 15:
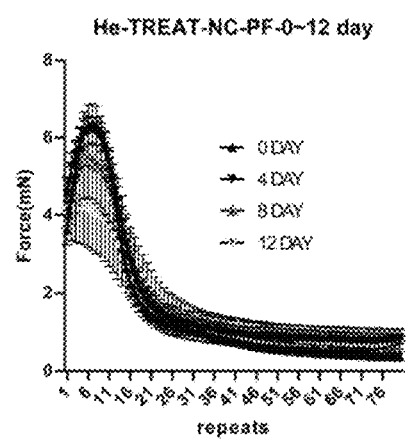
FIG. 15 shows the effect of *Chaenomelis fructus* extract on muscle fatigue induced by tonic fatigue contractions. Forced fatigue tolerance assessment of 80 times of low-frequency continuous stimulation of posterior tibialis muscle in BAG3 P209L/+ mice administered with saline for control group (A), 150 mg/kg/day *Chaenomelis fructus* extract (B) and 300 mg/kg/day *Chaenomelis fructus* extract (C). (n=5 for each group) *, p<0.05. **, p<0.01.
Figure 15:
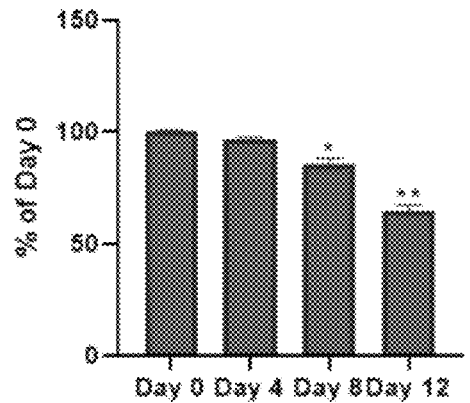
Figure 15:
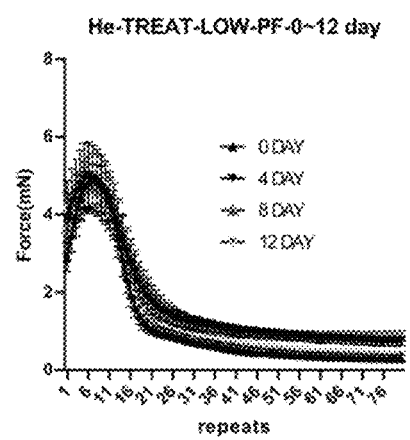
Figure 15:
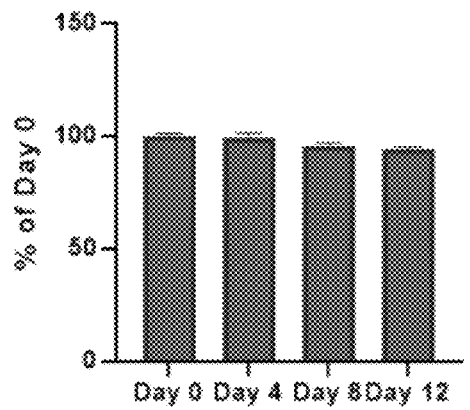
Figure 15:
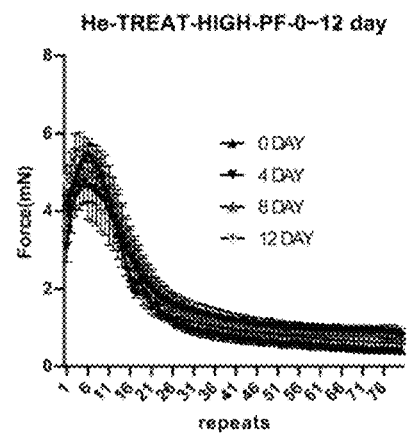
Figure 15:
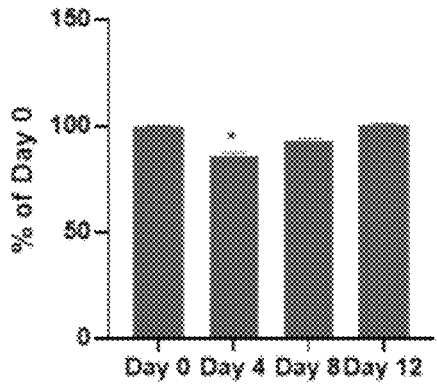
Figure 16:
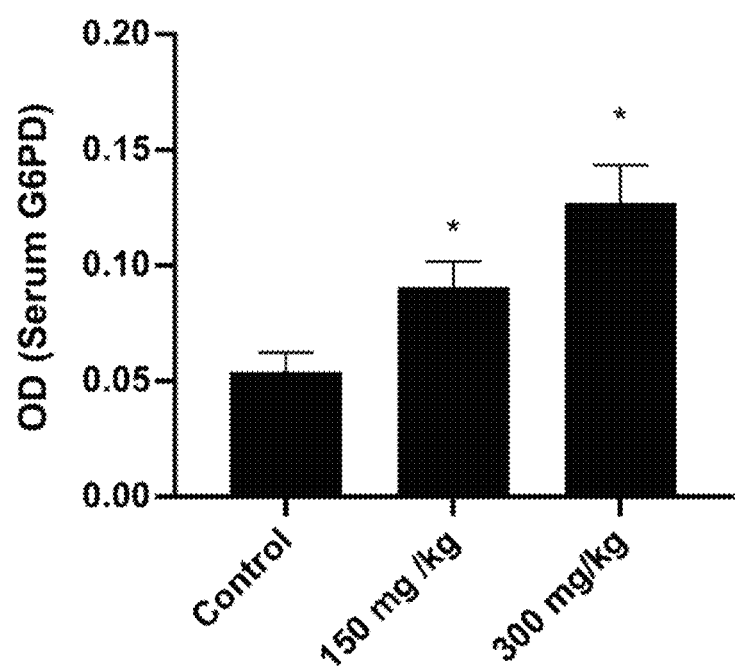
FIG. 16 shows the change of G6PD level in the serum of BAG3 P209L/+ mice orally administrated with *Chaenomelis fructus* extract (150 mg/kg and 300 mg/kg) for 12 days. (n=5 for each group) *, p<0.05.

In vivo experiment was conducted on the BAG3 P209L/+ mouse by *Chaenomelis fructus* extract administration and short-interval continuous low-frequency stimulation of the posterior tibialis muscle. The control group of BAG3 P209L/+ mice showed equivalent peak contractility in the training cycles of Day 0 and Day 12, with a significantly decrease in Day 8 and Day 12. (FIG. 15A). In the group of 150 mg/kg *Chaenomelis fructus* extract treated BAG3 P209L/+ mice, the peak contractility of the posterior tibialis muscle was unchanged in all the 4 training cycles (FIG. 15B). In the group of 150 mg/kg *Chaenomelis fructus* extract treated BAG3 P209L/+ mice, it was shown that the peak contractile force of the posterior tibial muscle decreased slightly on days 4, while no significantly changes on Day 8 and Day 12 compared with Day 0 (FIG. 15C). The results suggest that *Chaenomelis fructus* extract can alleviate the contraction power decay of the posterior tibialis muscle due to the accumulation of motor injury and improve the ability to recover contractile force. As expected, serum G6PD levels in the BAG3 P209L/+ mice were significantly increased by *Chaenomelis fructus* extract (FIG. 16).

What is claimed is:

1. A method of treating a glucose-6-phosphate dehydrogenase (G6PD) deregulated disorder in a subject in need thereof, the method comprising administering a therapeutically effective amount of oleanolic acid, a pharmaceutically acceptable salt thereof, or a prodrug thereof to the subject, wherein the G6PD deregulated disorder is BCL2 associated athanogene myofibrillar myopathy Bag3opathy).

2. The method of claim 1, wherein the subject suffers from one or more of severe muscle weakness, cardiomyopathy, and respiratory insufficiency.

3. The method of claim 1, wherein the oleanolic acid or a pharmaceutically acceptable salt thereof is administered to the subject in the form of a botanical product or an extract thereof.

4. The method of claim 3, wherein the botanical product comprises one or more of *Crataegi fructus, Forsythiae fructus, Prunellae spica, Verbenae herba, Eriobotryae folium, Ligustri lucidi fructus, Kaki calyx, Chaenomelis fructus, Jujubae fructus, Corni fructus*, or an extract thereof.

5. The method of claim 3, wherein the botanical product comprises *Chaenomelis fructus* or an extract thereof.

6. The method of claim 5, wherein the *Chaenomelis fructus* extract is prepared by contacting *Chaenomelis fructus* with ethanol thereby extracting at least a portion of the oleanolic acid or a pharmaceutically acceptable salt thereof present in the *Chaenomelis fructus* and forming an ethanol extract comprising oleanolic acid or a pharmaceutically acceptable salt thereof and optionally removing ethanol from the ethanol extract thereby forming the *Chaenomelis fructus* extract.

7. The method of claim 1, wherein the subject has a BCL2 Associated Athanogene 3 (BAG3) gene comprising a c.626C>T mutation.

8. The method of claim 1, wherein the prodrug of oleanolic acid has the chemical formula 2:

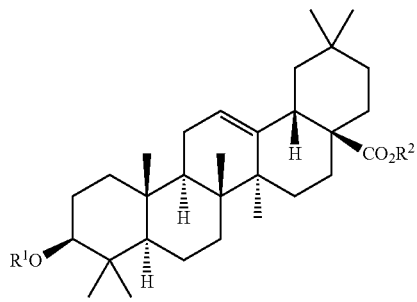

or a pharmaceutically acceptable salt thereof, wherein
$R^1$ is hydrogen, R(C=O)— or RO(C=O)—;
$R^2$ is hydrogen, alkyl, cycloalkyl, aralkyl, or aryl; and
R for each instance is independently hydrogen, alkyl, aralkyl, aryl, or heterocycloalkyl, wherein at least one $R^1$ and $R^2$ is not hydrogen.

9. The method of claim 1, wherein the subject is a human.

* * * * *